US012752085B2

(12) United States Patent
Nageswaran et al.

(10) Patent No.: US 12,752,085 B2
(45) Date of Patent: Oct. 6, 2026

(54) GUIDEWIRE INCLUDING AN ELONGATED BODY WITH A FLEXIBLE DISTAL SECTION

(71) Applicant: Covidien LP, Mansfield, MA (US)

(72) Inventors: Ashok R. Nageswaran, Irvine, CA (US); Daniel J. Deen, Long Beach, CA (US)

(73) Assignee: Covidien LP, Mansfield, MA (US)

( * ) Notice: Subject to any disclaimer, the term of this patent is extended or adjusted under 35 U.S.C. 154(b) by 330 days.

(21) Appl. No.: 18/645,022

(22) Filed: Apr. 24, 2024

(65) Prior Publication Data

US 2024/0358977 A1 Oct. 31, 2024

Related U.S. Application Data

(60) Provisional application No. 63/499,005, filed on Apr. 28, 2023.

(51) Int. Cl.
*A61M 25/09* (2006.01)

(52) U.S. Cl.
CPC ....................... *A61M 25/09* (2013.01); *A61M 2025/09075* (2013.01)

(58) Field of Classification Search
CPC ........ A61M 25/09; A61M 2025/09075; A61M 2025/09133; A61B 5/6851; A61B 2017/22038; A61B 18/1492
See application file for complete search history.

(56) References Cited

U.S. PATENT DOCUMENTS

| | | | |
|---|---|---|---|
| 6,004,279 | A | 12/1999 | Crowley et al. |
| 6,048,338 | A | 4/2000 | Larson et al. |
| 7,708,704 | B2 | 5/2010 | Mitelberg et al. |
| 7,981,091 | B2 | 7/2011 | Root et al. |
| 8,419,658 | B2 | 4/2013 | Eskuri |
| 8,454,535 | B2 | 6/2013 | Majercak et al. |
| 8,460,213 | B2 | 6/2013 | Northrop |

(Continued)

FOREIGN PATENT DOCUMENTS

| | | | |
|---|---|---|---|
| AU | 2020264056 | A1 | 11/2021 |
| EP | 3799917 | B1 | 2/2023 |

(Continued)

OTHER PUBLICATIONS

International Preliminary Report on Patentability from International Application No. PCT/US2024/026447 dated Oct. 16, 2025, 8 pp.

(Continued)

*Primary Examiner* — Jason M Sims
*Assistant Examiner* — Noah M Healy
(74) *Attorney, Agent, or Firm* — Shumaker & Sieffert, P.A.

(57) ABSTRACT

A guidewire comprising: a core wire defining a longitudinal axis; and an elongated body extending along the longitudinal axis, the elongated body defining: an inner lumen configured to retain a distal portion of the core wire and a plurality of openings, wherein each opening of the plurality of openings defines an arc defining a radius of curvature and a concave portion facing a distal end of the elongated body or a proximal end of the elongated body, and wherein the radii of curvature of the plurality of openings varies along the longitudinal axis.

20 Claims, 11 Drawing Sheets

(56) References Cited

U.S. PATENT DOCUMENTS

| | | | | |
|---|---|---|---|---|
| 8,551,020 | B2 | 10/2013 | Chen et al. | |
| 8,784,337 | B2 | 7/2014 | Voeller et al. | |
| 8,795,254 | B2 | 8/2014 | Layman et al. | |
| 8,932,235 | B2 | 1/2015 | Jacobsen et al. | |
| 10,525,231 | B2 | 1/2020 | Moquin et al. | |
| 10,561,820 | B2 | 2/2020 | Sullivan et al. | |
| 10,617,847 | B2 | 4/2020 | Cottone et al. | |
| 10,933,221 | B2 * | 3/2021 | Lepak ............... | A61M 25/0138 |
| 11,083,870 | B2 | 8/2021 | Rottenberg et al. | |
| 11,207,502 | B2 | 12/2021 | Lippert et al. | |
| 2003/0093059 | A1 | 5/2003 | Griffin et al. | |
| 2006/0100687 | A1 | 5/2006 | Fahey et al. | |
| 2008/0077049 | A1 | 3/2008 | Hirshman | |
| 2008/0147170 | A1 | 6/2008 | Vrba | |
| 2009/0157048 | A1 | 6/2009 | Sutermeister et al. | |
| 2009/0204197 | A1 | 8/2009 | Dorn et al. | |
| 2012/0078285 | A1 | 3/2012 | Griffin | |
| 2014/0214007 | A1 * | 7/2014 | Kimura ............. | A61M 25/0054 604/528 |
| 2014/0276117 | A1 | 9/2014 | Burkett | |
| 2017/0296221 | A1 * | 10/2017 | Di Caprio ............. | A61M 25/01 |
| 2018/0228502 | A1 | 8/2018 | Shaffer et al. | |
| 2019/0232018 | A1 | 8/2019 | Fojtik | |
| 2019/0255290 | A1 | 8/2019 | Snyder et al. | |
| 2020/0023164 | A1 | 1/2020 | Tran et al. | |
| 2020/0230359 | A1 | 7/2020 | Fojtik et al. | |
| 2021/0093832 | A1 | 4/2021 | Beeckler et al. | |
| 2021/0145511 | A1 | 5/2021 | Marchand et al. | |
| 2021/0346656 | A1 | 11/2021 | Lippert et al. | |
| 2022/0211981 | A1 * | 7/2022 | Darbellay ......... | A61M 25/0147 |

FOREIGN PATENT DOCUMENTS

| | | | |
|---|---|---|---|
| IN | 202121006813 | A | 2/2021 |
| WO | 2020217171 | A1 | 10/2020 |

OTHER PUBLICATIONS

International Search Report and Written Opinion of International Application No. PCT/US2024/026447 dated Sep. 9, 2024, 11 pp.

U.S. Appl. No. 18/644,808, filed Apr. 24, 2024, by Nageswaran et al.

* cited by examiner

GUIDEWIRE INCLUDING AN ELONGATED BODY WITH A FLEXIBLE DISTAL SECTION

This application claims the benefit of U.S. Provisional Patent Application No. 63/499,005, filed Apr. 28, 2023, and entitled "GUIDEWIRE INCLUDING AN ELONGATED BODY WITH A FLEXIBLE DISTAL SECTION," the entire contents of which is incorporated herein by reference.

TECHNICAL FIELD

This disclosure relates to a medical guidewire.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels. A medical guidewire may be disposed within the catheter lumen and is configured to control navigation of the medical catheter within the body of a patient.

SUMMARY

In some examples, a guidewire includes an elongated body comprising a proximal section and a distal section, the distal section including a wall defining one or more openings. The one or more openings extend at least partially through a thickness of the inner wall of the elongated body. The guidewire may also include one or more other elements, such as, but not limited to, an outer jacket, a core wire, and a support member (e.g., a coil and/or a braid). The one or more openings defined in the wall of the distal section of the elongated body may increase a bending flexibility of the distal section relative to the proximal section of the elongated body. The one or more openings may also cause the distal section of the elongated body to have increased bending flexibility without reducing tensile strength below a threshold for navigability through the vasculature. This disclosure also describes examples of methods of forming the elongated bodies disclosed herein and methods of using guidewires having the example elongated bodies.

In some examples, this disclosure describes a guidewire comprising: a core wire defining a longitudinal axis; and an elongated body extending along the longitudinal axis, the elongated body defining: an inner lumen configured to retain a distal portion of the core wire and a plurality of openings, wherein each opening of the plurality of openings defines an arc defining a radius of curvature and a concave portion facing a distal end of the elongated body or a proximal end of the elongated body, and wherein the radii of curvature of the plurality of openings varies along the longitudinal axis.

In some examples, this disclosure describes a method of manufacturing a guidewire, the method comprising: determining placement of a plurality of openings along an outer surface of an elongated body; determining a radius of curvature for each opening of the plurality of openings; and forming the plurality of openings into the outer surface of the elongated body, each opening defining a corresponding determined radius of curvature.

In some examples, this disclosure describes a guidewire comprising: a core wire; and an elongated body extending along a longitudinal axis, the elongated body defining: an inner lumen, wherein the distal portion of the core wire is positioned within the inner lumen; and a plurality of openings disposed along the elongated body between a distal end of the elongated body and a proximal end of the elongated body, wherein each opening of the plurality of openings defines an arc define a radius of curvature and extending from a first end to a second end, wherein the first end and the second end are disposed at a same longitudinal position along the elongated body, and wherein for each arc, a center of the arc is disposed at a different longitudinal position than the first end and the second end of the arc, wherein the plurality of openings defines a plurality of rows of openings around a perimeter of the elongated body, wherein longitudinally adjacent rows of openings are separated by a longitudinal distance, and wherein the longitudinal distances between longitudinally adjacent rows and the radii of curvature of the plurality of openings increase or decrease between the distal end and the proximal end.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
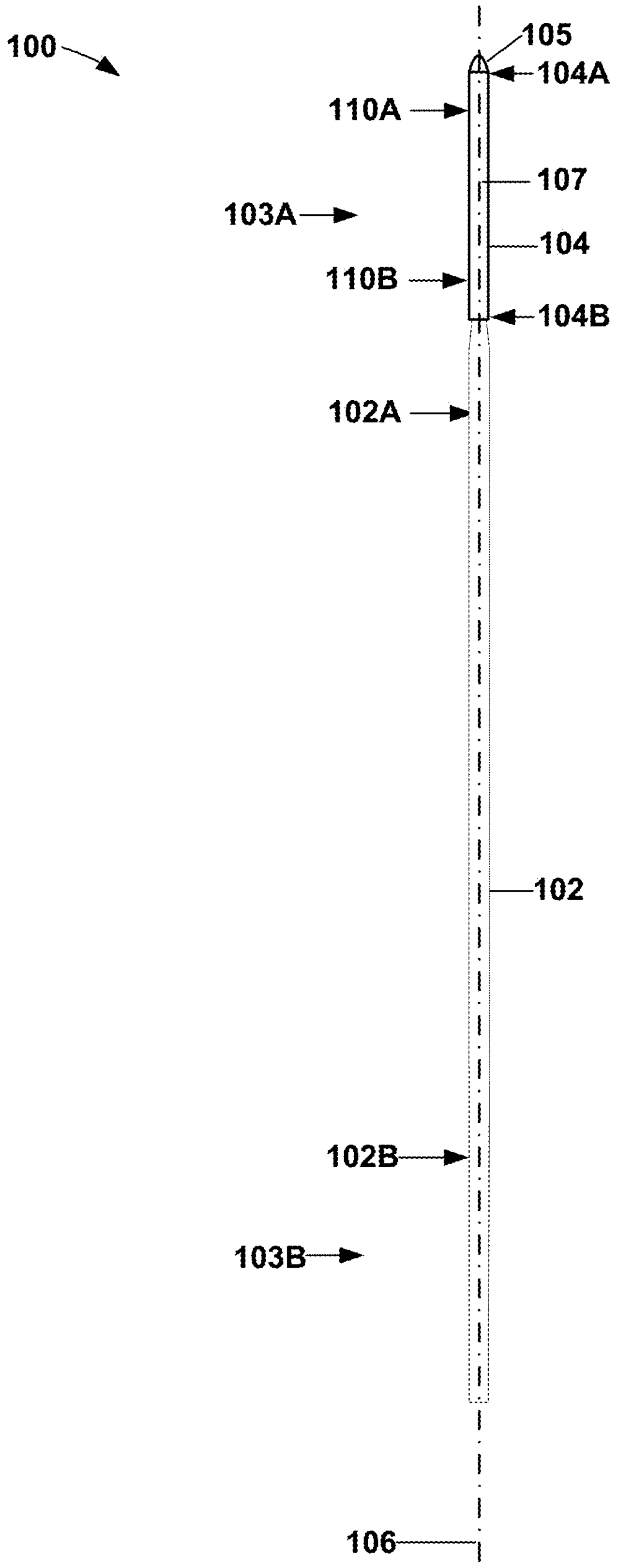
FIG. 1 is a conceptual diagram illustrating example guidewire having an elongated body defining one or more openings in the wall of the elongated body.

In some examples, medical devices described herein may be used with a medical catheter ("catheter") that includes a relatively flexible catheter body configured to be navigated through vasculature of a patient, e.g., tortuous vasculature in a brain of the patient. The catheter may be navigated within the vasculature via use of a medical guidewire ("guidewire"). The guidewire includes a relatively flexible distal section that may exhibit increased flexibility relative to a proximal section of the guidewire. In some examples, the guidewire includes an elongated body (also referred to herein as "elongated tube") and an outer jacket, and the increased flexibility of the distal section may be at least partially (e.g., partially or fully) attributable to the configuration of the elongated body. For example, a distal section of the elongated body may include one or more openings (also referred to herein as "voids" and/or "cuts"), which help to increase a bending flexibility of the distal section of the elongated body while maintaining a desirable tensile strength of the elongated body. The one or more openings may have any suitable configuration that helps to increase the bending flexibility of the elongated body while maintaining tensile strength of the elongated body and the overall guidewire. Each of the one or more openings may be an absence of material in or a locally thinner portion of the wall (e.g., a groove, divot, pocket, through-hole, or the like in an otherwise continuous surface), or may be an incision in the wall of the elongated body that is formed without removing material from the wall.

While the examples of this disclosure primarily describe the elongated body and the openings on the elongated body with reference to a guidewire, an elongated body as described in any of the examples included herein may be used in other medical applications, e.g., as an inner liner or a support member in a medical catheter, or the like.

The elongated body or guidewire body may require a minimum tensile stiffness and/or minimum tensile strength for a particular use of the guidewire. Inadequate tensile stiffness or strength can translate into poor navigability of the guidewire through vasculature of a patient when a clinician is advancing and retracting the guidewire in tortuous anatomy. For example, if a distal tensile stiffness of the elongated body is inadequate, then the distal end of the guidewire may not retract from the patient at the same rate as the proximal section, which may reduce the control over the guidewire perceived by the clinician. In addition, if the tensile stiffness of the elongated body is inadequate, then the distal end of the guidewire may remain in place while the proximal end stretches away from it, which may cause a distal section of the guidewire to break away from the rest of the guidewire.

The tensile strength and bending flexibility provided by the arrangement of the one or more openings in an elongated body described herein may translate into better navigability when a clinician is advancing or retracting the guidewire, such as in tortuous anatomy. For example, the tensile strength of the elongated bodies defining one or more openings described herein may be sufficient to enable the distal section of the elongated body to be retracted from a patient without compromising the structural integrity of the guidewire. Further, the tensile stiffness of the elongated bodies described herein may enable both the distal end and the proximal section of a guidewire including one of the elongated bodies to be retracted from the vessel of a patient at the same rate, which may provide the clinician with a perception of more control over the guidewire.

By using the devices and techniques herein, the elongated body may have a sufficient tensile strength to allow a clinician to safely retract a distal section of the elongated body, even if, for example, the blood vessel around the distal end of the guidewire is constricting the guidewire. The tensile strength of the elongated body may help ensure that a distal section of the elongated body does not separate from a proximal the elongated body, e.g., during a medical procedure.

An elongated body may include a wall that defines an inner lumen and an outer surface of the elongated body. Each opening in the elongated body may extend at least partially through the wall, e.g., at least partially through a thickness of the wall or all the way through a thickness of the wall so as to expose an inner lumen of the elongated body. The thickness of the wall may be measured in a direction orthogonal to the longitudinal axis of the elongated body. In some examples, the wall may be thinner at an opening, which may allow for more flexibility of the elongated body at the region including and adjacent to the opening.

In some examples in which the one or more openings extend only partially through a thickness of a wall of an elongated body (also referred to herein as "partial cuts" or "partial openings"), the partial openings may be defined by an outer surface of the wall. For example, the partial openings may extend from the outer surface of the wall towards the inner lumen but may not extend all the way through the wall to the inner lumen of the elongated body. By positioning the partial openings on an outer surface of the wall, an inner surface of the elongated body may remain substantially smooth (e.g., smooth or nearly smooth, or without projections or indentations that would inhibit the passage of a medical device), which may facilitate passage of one or more medical devices (e.g., guide members, an embolic protection device or an embolic retrieval device, and the like) through the inner lumen of the elongated body. In other examples, however, the partial openings may be defined by an inner surface of the wall in addition to, or instead of, the outer surface. In some examples in which the one or more openings extend fully through a thickness of a wall of an elongated body, (also referred to herein as "though cuts" or "through openings"), the one or more openings may be arranged so as not to divide the elongated body into physically separate portions. For example, the openings may not extend around the entire perimeter or circumference of the elongated body.

The one or more openings defined by a distal section of an elongated body may be arranged in one or more patterns as described in further detail below. In some examples, the one or more openings may be arranged in mirror patterns, wherein longitudinally adjacent openings define reflectional symmetry and/or are mirror images about a reference axis. The reference axes may be orthogonal to the longitudinal axis or may be separated from the longitudinal axis by an angle less than 90 degrees. Such mirror patterns may reduce a pitch between adjacent openings, thereby increasing a density of the openings and increasing a bending flexibility of the elongated body. In some examples, the one or more openings may define one or more arcs defining varying radii of curvature. In such examples one or more openings at a more proximal section of the elongated body may have a different radius of curvature than one or more openings at a more distal section of the elongated body. Such arcs may increase an overall length, and correspondingly tensile resistance, of the one or more openings while maintaining adequate integrity of the elongated body in response to torque. In some examples, one or more other dimensions of the one or more openings may vary along the length of the elongated body between the distal end and the proximal end of the elongated body.

An elongated body described herein includes a distal section including the one or more openings, and a proximal section. In some examples, the elongated body may consist essentially of the proximal and distal sections. In some examples, the distal section is immediately adjacent to and mechanically connected to the proximal section (e.g., formed integrally with the proximal section or formed separate from the proximal section and attached thereto). The distal section of the elongated body may include a plurality of regions. The plurality of regions may be arranged longitudinally along the length of the distal section. Each of the plurality of regions may include openings having the same characteristics and/or dimensions. For example, openings in a first region may define a same radius of curvature. In another example openings in a first region may all orient towards one end of the elongated body (e.g., the distal end or the proximal end) and the first region may be a mirror image of a longitudinally adjacent region.

In some examples, a guidewire including the elongated body comprising a distal section defining one or more openings may be a variable stiffness guidewire that increases in flexibility from a proximal end towards a distal end. For example, a proximal section of the elongated body may not include any openings or may have an arrangement of openings (e.g., fewer openings, a different pattern, or different dimensions) different from that of the distal section, such that the distal section is more flexible than the proximal section. In this way, the openings defined in the distal section of the elongated body may configure the distal section to be more flexible than a more proximal section of the elongated body. The variable stiffness may allow the guidewire to exhibit a relatively high level of pushability due to the stiffer proximal section of the elongated body which contributes to the overall stiffness of the guidewire, and exhibit a relatively high level of flexibility at the distal section of the guidewire due at least in part to the configuration of the distal section of the elongated body.

In some examples, a guidewire described herein includes an elongated body, a support element (e.g., a coil member or a braided member, or combinations thereof), a core member (e.g., a core wire) and an outer jacket, which can interact to provide a relatively flexible elongated body with sufficient structural integrity (e.g., column strength, which may be a measure of a maximum compressive load that can be applied to the elongated body without taking a permanent set) to permit the guidewire to be advanced through the vasculature via a pushing force applied to a proximal section of the guidewire, e.g. without buckling, kinking, or otherwise undesirably deforming (e.g., ovalization). A distal section of the guidewire may lead the guidewire through vasculature of a patient. The example elongated bodies described herein may increase the flexibility of the distal section of the guidewire, and, therefore, may increase the navigability of the guidewire through vasculature compared to a guidewire including an elongated body that is otherwise the same, but does not include the one or more openings in a distal section. The elongated body may be formed from a biocompatible metallic alloy, e.g., Nitinol. The metallic alloy may be formed into an elongated tube (e.g., a hypotube or the like) defining the elongated body. In some examples, the elongated body may be formed from one or more polymers (e.g., Polytetrafluoroethylene (PTFE) or the like) into an elongated tube.

The guidewires described herein can be configured to exhibit a relatively high level of flexibility, pushability, torqueability (e.g., torque responsiveness), and/or structural integrity. In some examples, a guidewire includes an elongated body including a distal section defining one or more openings, a structural support member, and an outer jacket, which interact to provide a flexible guidewire with sufficient structural integrity (e.g., column strength) to permit the guidewire to be advanced through the vasculature from a pushing force applied to a proximal section of the guidewire, without buckling or undesirable bending (e.g., kinking) of the guidewire. In some examples, the flexible guidewire is configured to substantially conform to the curvature of the vasculature. In addition, in some examples, the guidewire may define a column strength and flexibility that allow at least a distal section of the guidewire to be navigated from a femoral artery, through the aorta of the patient, and into the intracranial vascular system of the patient, e.g., to reach a relatively distal treatment site, including the middle cerebral artery (MCA), internal carotid artery (ICA), the Circle of Willis, and tissue sites more distal than the MCA, ICA, and the Circle of Willis. The MCA and, consequently, vasculature distal to the MCA may be relatively difficult to access due to the carotid siphon anatomy that must be traversed to reach such locations.

Although primarily described as being used to reach relatively distal vasculature sites, the guidewires described herein may readily be configured to be used with other target tissue sites. For example, the guidewire may be used to access tissue sites throughout the coronary and peripheral vasculature, the gastrointestinal tract, the urethra, ureters, Fallopian tubes, and other body lumens.

FIG. 1 is a conceptual diagram illustrating example guidewire 100. Guidewire 100 may define a longitudinal axis 106 extending between a distal section 103A and a proximal section 103B. As shown, guidewire 100 includes a core wire 102, an elongated body 104, and an atraumatic tip 105. Core wire 102 extends along longitudinal axis 106 of guidewire 100 between a distal section 102A and a proximal section 102B. Elongated body 104 extends along longitudinal axis 106 between a distal end 104A and a proximal end 104B, and defines an inner lumen. Distal end 104A may be coupled to atraumatic tip 105 and/or to core wire 102. Core wire 102 may be disposed within the inner lumen defined by elongated body 104. Elongated body 104 may be configured to retain distal section 102A of core wire 102, such that elongated body 104 is mechanically responsive to a force exerted on proximal section 102B of core wire 102. For example, elongated body 104 may be configured to retain distal section 102A of core wire 102 within the inner lumen defined by elongated body 104. As described in greater detail below, elongated body 104 may define one or more openings in a wall of elongated body 104.

Guidewire 100 may define a suitable length for accessing a target tissue site within the patient from a vascular access point. The length may be measured along longitudinal axis 106 of guidewire 100. The target tissue site may depend on the medical procedure for which guidewire 100 and/or an accompanying catheter is used. For example, if the catheter is a distal access catheter used to access vasculature in a brain of a patient from a femoral artery access point at the groin of the patient, guidewire 100 may have a length of at least about 125 centimeters (cm) to about 135 cm, such as about 132 cm, although other lengths may be used. Distal section 103A of guidewire 100 may be disposed within the vasculature of the patient and proximal section 103B may be disposed outside of the body of the patient. A clinician may manipulate proximal section 103B of guidewire 100 to rotate, retract, and/or advance distal section 103A of guidewire 100 within the vasculature.

Guidewire 100 may be used to access relatively distal locations in a patient, such as the middle cerebral artery ("MCA") in a brain of a patient. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Guidewire 100 may be structurally configured to be relatively flexible, pushable, and relatively kink- and buckle-resistant, so that it may resist buckling when a pushing force is applied to a relatively proximal section of the catheter to advance the catheter body distally through vasculature, and so that it may resist kinking when traversing around a tight turn in the vasculature. Kinking or buckling of guidewire 100 may hinder a clinician's efforts to push the catheter body distally, e.g., past a turn. Such kinking or buckling of guidewire 100 may be more likely at distal portion 103A of guidewire 100, as distal portion 103A may experience relatively larger bending forces than proximal portion 103B as both a leading portion of guidewire 100 and a distal-most portion of guidewire 100 positioned in vasculature that may become progressively more tortuous from the vascular access point to the target tissue site.

As discussed in further detail below, one structural characteristic that may contribute to at least the flexibility of guidewire 100, particular at distal portion 103A, is flexibility of elongated body 104. The flexibility of elongated body 104 may be based at least in part on a cut pattern of the one or more openings defined in a wall 107 of distal section 103A. The one or more openings in distal section 103A of elongated body 104 may improve the navigability of guidewire 100 through vasculature of a patient relative to another guidewire including an elongated body without any openings in the wall of the elongated body. Without being limited to any particular theory, a bending force exerted on guidewire 100 may cause guidewire 100 to bend away from longitudinal axis 106. For example, the bending force may cause guidewire 100 to bend along a plane orthogonal to longitudinal axis 106. The bending force may generate a compressive force in a portion of guidewire 100 facing toward the bending direction of guidewire 100 and a tensile force in a portion of guidewire 100 facing away from the bending direction. As compared to an identical elongated body with no openings, the one or more openings on elongated body 104 may provide discontinuities for reducing the generated tensile force (e.g., voids or cuts) and/or provide spaces for reducing the generated compressive force (e.g., voids), such that elongated body 104 may provide a reduced resistance to the bending force as compared to the identical elongated body that does not include any openings.

Core wire 102 may extend from atraumatic tip 105 to a proximal end of proximal portion 102B. During navigation of core wire 102 within vasculature of the patient, a distal section 102A may be disposed within the vasculature and a proximal section 102B may be outside of the body of the patient. A clinician may operate proximal section 102B to advance, retract, rotate, and/or bend guidewire 100 within the vasculature. Core wire 102 may transmit forces and/or torques applied, for example by the clinician to proximal section 102B along longitudinal axis 106 to atraumatic tip 105. At least a portion of distal section 102A is disposed within the inner lumen defined by elongated body 104 and transmits forces and/or torques from proximal section 102B to atraumatic tip 105. Core wire 102 may be formed from one or more biocompatible metallic alloys including, but is not limited to, stainless steel. Core wire 102 may be selected for a variety of properties, including mechanical strength sufficient to maintain integrity and transmit forces from distal section 102B to proximal section 102A, and flexibility sufficient for core wire 102 to be positioned within a more proximal portion of the pathway in the vasculature. However, the mechanical strength of core wire 102 may be substantially higher than required for forces experienced at distal portion 103A.

Elongated body 104 is configured with a higher flexibility than core wire 102 while maintaining adequate mechanical strength. Elongated body 104 defines one or more opening(s) on outer surface of elongated body 104 from distal end 104A to proximal end 104B. The opening(s) may have varied patterns, dimensions, and/or designs between distal end 104A and proximal end 104B, e.g., to increase flexibility of distal section 110A of elongated body 104 relative to proximal section 110B of elongated body 104. For example, during navigation of the catheter through relatively tortuous vasculature, distal section 103A of guidewire 100 may experience forces along axis 106 (e.g., tensile or compressive forces), forces around axis 106 (e.g., torque), and/or forces away from axis 106 (e.g., bending forces). A distal section of an identical elongated body that does not include opening(s) may provide resistance to these forces. While resistance to forces along and around axis 106 may ensure sufficient pushability of guidewire 100, resistance to forces away from axis 106 may reduce navigability of guidewire 100. The openings may be configured to improve navigability of distal section 103A relative to an identical guidewire that does not include openings by reducing resistance of elongated body 104 to forces away from axis 106 without substantially reducing resistance of elongated body 104 to forces along and/or around axis 106 beyond that for maintaining pushability of elongated body 104. For example, a flexibility of distal section 103A of elongated body 104 that includes openings may be lesser than or equal to half a flexibility of an identical elongated body that does not include openings. An identical elongated body may be a metallic (e.g., a stainless steel) round wire of equivalent dimensions that does include any openings. In some examples, distal section 110A including openings is at least as flexible as a round metallic wire without openings that defines a larger outer diameter than distal section 110A.

In some examples, elongated body 104 includes opening(s) having individual, relative, and/or collective properties configured to provide increased flexibility to elongated body 104 as compared to an identical elongated body without any openings. For example, individual properties may include properties of an individual opening, such as size or shape; relative properties may include properties of two or more openings or groups of openings relative to each other, such as pitch; and collective properties may include properties of a plurality of the openings, such as a density of the openings, and/or flexibility of distal section 110A or portion of distal section 110A provided by the openings.

In some examples, elongated body 104 includes opening(s) arranged in a particular pattern configured to provide increased flexibility to elongated body 104 as compared to an identical elongated body without any openings. A pattern of the one or more openings may be selected to achieve a threshold level of structural integrity (e.g., a threshold bending stiffness, a threshold tensile strength, a threshold torqueability), while increasing the flexibility of distal section 110A of elongated body 104 relative to the distal section of an identical elongated body without any openings. The pattern of the one or more openings may define varied arrangements and/or dimensions from a distal end 104A to a proximal end 104B of elongated body 104, e.g., to increase flexibility distal section 110A of elongated body 104 while maintaining the tensile strength of distal section 110A.

Each opening on elongated body 104 may define a continuous arc along an outer surface of wall 107 of elongated body 104. Each arc may be a semicircular arc, a parabolic arc, an elliptical arc, or the like. Each arc may define a concave portion extending towards distal end 104A or proximal end 104B of elongated body 104. Each arc may be defined along a plane in line with longitudinal axis 106, e.g., such that each arc defines ends having a same longitudinal position and a center of the arc having a different longitudinal position than the ends of the arc. The arc of each opening may be defined by a radius of curvature. For example, an arc length of each opening is defined by the respective radius of curvature for the arc. In some examples, the openings may define varying radii of curvature along the length of elongated body 104 from distal end 104A to proximal end 104B.

In some examples, some of the openings may be mirror images of other openings. In such example, one or more openings are mirror images of one or more other openings across a reference axis orthogonal to longitudinal axis 106. Mirroring at least some of the openings may increase density of openings on elongated body 104 (e.g., may reduce a longitudinal distance between longitudinally adjacent openings) without altering other dimensions of the openings (e.g., the radii of curvature of openings). Increasing the density of openings on portions of elongated body 104 (e.g., on distal section 110A of elongated body 104) may increase the flexibility of the portions of elongated body 104 as compared to an identical elongated body without mirroring openings.

Opening(s) may be arranged in circumferential rows around the outer surface of elongated body 104. In some examples, each circumferential row of openings is disposed along a reference plane orthogonal to longitudinal axis 106. In some examples, one or more circumferential rows of openings are offset from a longitudinally adjacent circumferential row of openings. For example, each opening in a first circumferential row of openings is circumferentially offset from a corresponding opening in a longitudinally adjacent second circumferential row of openings by a circumferential offset angle. The circumferential offset of longitudinally adjacent circumferential rows of openings may inhibit preferential bending of elongated body 104 along specific planes. In some examples, elongated body 104 includes openings shaped and/or positioned to locally increase a flexibility of a portion of elongated body 104 at or near the particular opening.

Each opening may be defined by a set of corresponding dimensions including a length, a width, a beam length, a pitch, a radius of curvature, an angular offset angle, and a circumferential offset angle. A pitch of each opening defines a longitudinal distance between longitudinally alternate openings. A beam length of openings defines an uncut length of elongated body 104 between a first end of one opening and a second end of a circumferentially adjacent opening. Beam lengths may be measured along a reference plane orthogonal to longitudinal axis 106. The angular offset angle defines an offset angle between two longitudinally alternate openings and/or between corresponding openings of longitudinally separated patterns of openings along the longitudinal length of elongated body 104. The angular offset angles of openings may define a rotational pitch between openings and/or repeating patterns of openings. The openings and/or repeating patterns of openings may define one or more helical or spiral patterns along the longitudinal length of elongated body 104, each helical or spiral pattern defined by a corresponding rotational pitch. For example, the openings and/or repeating patterns of openings may define a helix or spiral of openings extending around the outer surface of wall 107 and along longitudinal axis 106. Each dimension may vary along the length of elongated body 104 or along the length of certain sections of elongated body 104, e.g., to change the flexibility and tensile strength of certain sections of elongated body 104 relative to other sections of elongated body 104. For example, openings at distal end 104A define different beam lengths, pitches, radii of curvature, circumferential offset angles, and/or angular offset angles than other openings at proximal end 104B of elongated body 104.

Distal section 110A of elongated body 104 may define an increased density of openings relative to a more proximal section (e.g., proximal section 110B) of elongated body 104 by at least defining decreased beam lengths, pitches, and/or angular offset angles between openings and/or increased the radii of curvature of openings relative to openings on the more proximal section of elongated body 104. The increase density of openings may provide several material property benefits to distal section 110A of elongated body 104. The increased radii of curvature of openings and the reduced pitch between openings may increase tensile strength and torque response of elongated body 104 while causing distal section 110A to maintain a low bending stiffness. In some examples, the reduced pitch between openings reduces a bending radius of distal section 110A and/or reduce localized strain exerted upon any of the uncut sections of distal section 110A. Distal section 110A may define openings having a combination reduced beam lengths and pitches between openings to reduce bending stiffness and increase pliability of distal section 110A.

The measurements may be varied along the length of elongated body 104. For example, proximal section 110B may define an increased density of openings relative to distal section 110A. Increased density of openings at proximal section 110B may simplify manufacturing of proximal section 110B, thereby simplifying overall manufacturing complexity and manufacturing cost of elongated body 104.

In some examples, as illustrated in FIG. 1, at least some of opening(s) are mirror images of one or more other openings on elongated body 104. For example, one or more openings define reflectional symmetry of one or more other openings, e.g., the one or more openings are reflections of the one or more other openings across an axis or plane of reflection. The axis of reflection or plane of reflection may be orthogonal to longitudinal axis 106. A mirror image of one opening may be of an identically sized opening with a different orientation. In some examples, an opening is orientated towards one end of elongated body 104 and a mirror image of the opening is orientated towards the opposite end of elongated body 104. For example, an open section of a concave portion of the opening is orientated towards one end of elongated body 104 and an open section of a concave portion of the mirror image opening is orientated towards the opposite end of elongated body 104 Longitudinally adjacent openings may be mirror images across reference plane that are orthogonal to longitudinal axis 106 or that are offset from longitudinal axis 106 by a predetermined angle. In some examples, groups of openings (e.g., one or more circumferential rows of openings) may be mirror images of other groups of openings. each group of openings may be disposed within a region of the plurality of regions defined by elongated body 104. Each region may be a mirror image of another region of elongated body 104. As will be described further below, such mirroring of openings may enable a higher density of openings that have a non-linear shape, such as an arced shape, while maintaining a minimum distance (e.g., a minimum pitch) between openings, e.g., as compared to an identical elongated body 104 without mirrored openings.

Distal section 110A includes distal end 104A of elongated body 104, and proximal section 110B includes proximal end 104B of elongated body 104. Distal section 110A may have any suitable length. In some examples, distal section 110A is about 5% to about 50% of a total length of elongated body 104, such as about 10% to about 40%, about 5% to about 25%, or about 10% to about 25% of the total length of elongated body 104. In some examples, distal section 110A may define a length of about 5 cm to about 40 cm, such as about 5 cm to about 35 cm, or about 5 cm to about 10 cm. In some of these examples, elongated body 104 defines a total length of about 132 cm. Distal section 110A may be configured to provide a leading end for navigating through vasculature, while proximal section 110B may be configured to comply with changing curvature of the vasculature. As such, distal section 110A and proximal section 110B may be configured with different properties corresponding to the different functions of each section.

Atraumatic tip 105 may define a distalmost portion of guidewire 100. Atraumatic tip 105 may be configured to prevent adverse interaction between portions of guidewire 100 (e.g., distal end 104A of elongated body 104) and tissue of the patient as guidewire 100 navigates through the vasculature of the patient. The atraumatic tip 105 may define a blunted and/or semi-spherical shape, e.g., to prevent unintended puncture of the tissue of the patient. Atraumatic tip 105 may be formed from biocompatible materials including, but are not limited to, a biocompatible glue, a biocompatible polymer, or the like. Atraumatic tip 105 may be coupled to (e.g., permanently affixed to) both elongated body 104 and a distal end of core wire 102. For example, a relatively radially inward portion of a proximal end of atraumatic tip 105 is coupled to the distal tip of core wire 102 and a relatively radially outward portion of the proximal end of atraumatic tip 105 is coupled to the distal end of elongated body 104. Coupling atraumatic tip 105 to both core wire 102 and elongated body 104 may secure the position and orientation of elongated body 104 relative to core wire 102 and vice versa, e.g., to prevent unintended rotation and/or separation of elongated body 104 from core wire 102.

In some examples, an outer diameter of guidewire 100 may be uniform along the length of guidewire 100. In other examples, an outer diameter of guidewire 100 may taper from a first outer diameter at proximal section 102B of core wire 102 to a second outer diameter at distal section 102A of core wire 102, the second outer diameter being smaller than the first outer diameter. In some examples, the taper may be continuous along the length of guidewire 100, such that an outer surface of core wire 102 defines a smooth transition between different diameter portions. In some examples, as illustrated in FIG. 1, distal section 102A tapers to a smaller outer diameter such that when elongated body 104 is disposed over a reduced-diameter portion of distal section 102A of core wire 102, an outer diameter of elongated body 104 defines a same or smaller outer diameter as a portion of core wire 102 proximal to proximal end 104B of elongated body 104. In other examples, core wire 102 may define discrete step-downs in outer diameter to define the taper. The size of the discrete step-downs in diameter may be selected to reduce the number of edges that may catch on anatomical features within the vasculature and/or with the catheter as guidewire 100 is advanced through vasculature.

A larger diameter proximal section 102B of core wire 102 may provide better proximal support for core wire 102 than a smaller diameter proximal section 102B, which may help increase the pushability of guidewire 100. In addition, a smaller diameter distal section 102A of core wire 102 may increase the navigability of guidewire 100 through tortuous vasculature than a larger diameter distal section 102A. Thus, reducing the outer diameter of core wire 102 at distal section 102A may improve navigability of guidewire 100 through tortuous vasculature while still maintaining a relatively high level of proximal pushability as compared to an identical core wire 102 defining a larger diameter distal section 102A or defining a uniform outer diameter.

In some examples, at least a portion of an outer surface of guidewire 100 includes one or more coatings, such as, but not limited to, an anti-thrombogenic coating, which may help reduce the formation of thrombi in vitro, an anti-microbial coating, or a lubricating coating. The lubricating coating may be configured to reduce static friction or kinetic friction between guidewire 100 and tissue of the patient and/or a catheter retaining guidewire 100 as guidewire 100 is advanced through the vasculature. The lubricating coating can be, for example, a hydrophilic coating. In some examples, the entire working length of guidewire 100 (from atraumatic tip 105 to proximal section 102B of core wire 102) is coated with the hydrophilic coating. In other examples, only a portion of the working length of guidewire 100 coated with the hydrophilic coating. This may provide a length of guidewire 100, e.g., at proximal section 102B, with which the clinician may grip guidewire 100 (e.g., core wire 102), e.g., to rotate guidewire 100, pull guidewire 100, or push guidewire 100 through vasculature.

Figures 2A, 2B:
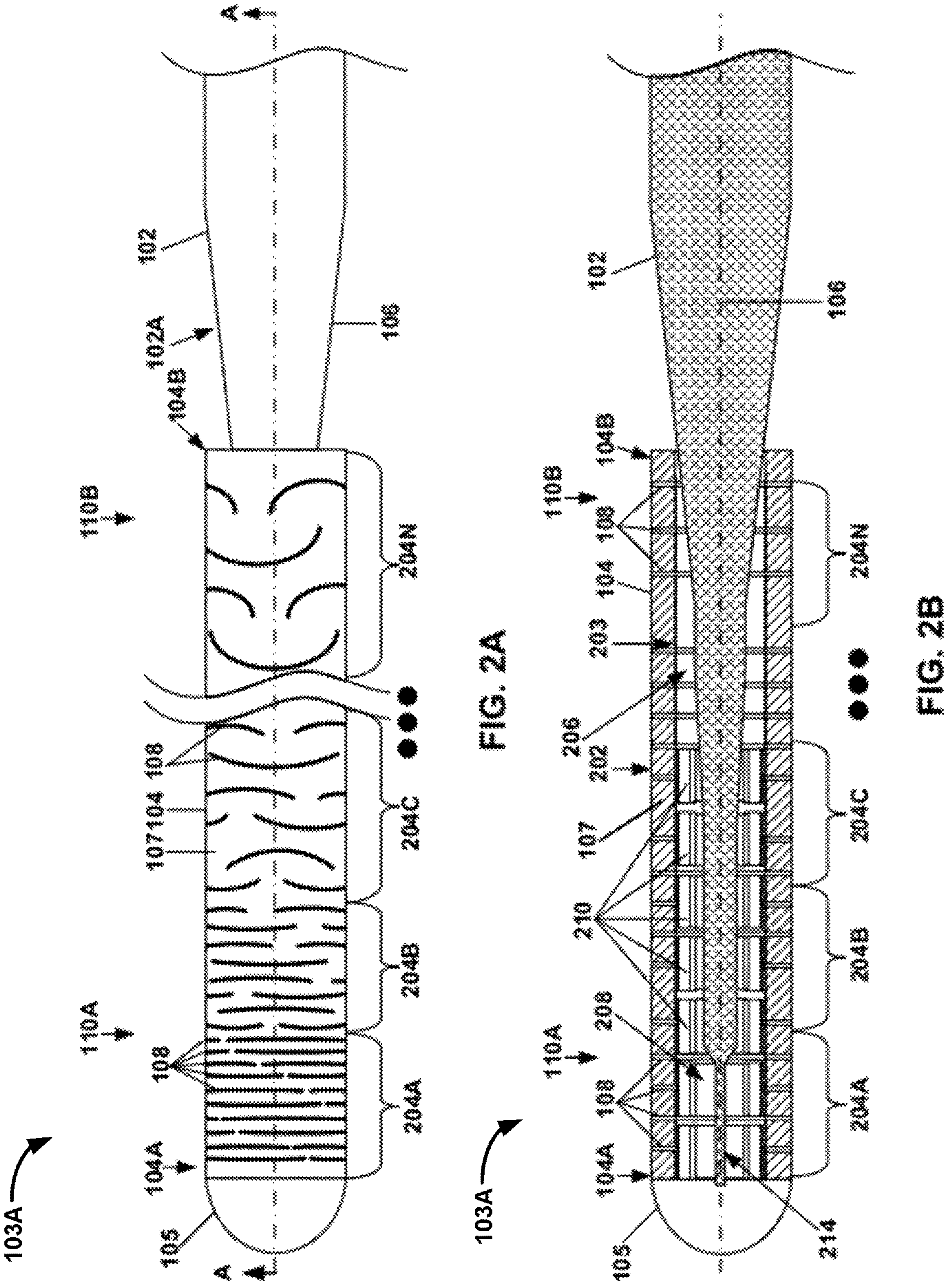
FIG. 2A is a conceptual diagram illustrating an elongated body of the example guidewire of FIG. 1.
FIG. 2B is a conceptual diagram illustrating a cross-sectional view of the distal section of the example guidewire of FIG. 2A, the cross-section being taken along line A-A in FIG. 2A.

FIG. 2A is a conceptual diagram illustrating a side view of elongated body 104 of guidewire 100 of FIG. 1. Elongated body 104 is disposed at distal section 103A of guidewire 100 and around distal section 102A of core wire 102 of guidewire 100. Elongated member 104 includes wall 107 extending along longitudinal axis 106 from distal end 104A to proximal end 104B. Distal end 104A may be coupled to atraumatic tip 105. A plurality of openings 108 are disposed within wall 107 of elongated body 104.

Openings 108 may include cuts, voids, or any other discontinuity in wall 107 that modifies an ability of at least a portion of elongated body 104 to compress or expand in response to an external force applied on elongated body 104. In some examples, at least one opening of openings 108 extends from an outer surface 202 of elongated body 104 to an inner surface of elongated body 104 defining an inner lumen of elongated body 104. In some examples, at least one opening of openings 108 extends partially from the outer surface of elongated body 104 towards the inner lumen of elongated body 104 without penetrating an inner surface of elongated body 104 defining the inner lumen.

Elongated body 104 may define a plurality of longitudinal regions 204A-204N (collectively referred to as "longitudinal regions 204" or "regions 204"). Longitudinal regions 204 may extend from distal end 104A to proximal end 104B. Each region of regions 204 may be longitudinally adjacent to one or more other regions of regions 204. For example, region 204B is longitudinally adjacent to and proximal to region 204A and longitudinally adjacent to and distal to region 204C. Each region 204 may include one or more openings 108 or circumferential rows of openings 108 around the outer perimeter of elongated body 104. Different groups of openings 108 may be disposed within longitudinal regions 204A-N. Each region 204 may define a different bending stiffness, a different tensile stiffness, or a different torqueability relative to another region 204 (e.g., a longitudinally adjacent region 204) in response to an external force of a same type and magnitude. Within each of regions 204, the dimensions of openings 108 within the respective region may remain uniform. For example, openings 108 within a single region 204 may define a same radius of curvature, pitch, beam length, or the like. The dimensions of openings 108 may vary between longitudinally adjacent regions 204. For example, each opening 108 within region 204B may define same dimensions and a first opening 108 within region 204B may define different dimensions than a second opening 108 within region 204A and a third opening 108 within region 204C. In some examples, one or more of regions 204 may be a mirror image of another of regions 204. For example, openings 108 in first region may be mirror images of openings 108 in a longitudinally adjacent second region across a reference plane between the first and second regions.

Each of regions 204 may be of a same longitudinal length along longitudinal axis 106. In some examples, at least two of regions 204 may have different longitudinal lengths. Each of regions 204 may have a same number of rows of openings 108 and/or a number of openings 108. In some examples, one or more regions 204 may include a single opening 108, two openings 108, or a single circumferential row of openings 108. In some examples, at least two of regions 204 may have a different number of rows of openings 108 and/or a different number of openings 108 within each region 204.

FIG. 2B is a conceptual diagram illustrating a cross-sectional view of distal section 103A of the example guidewire 100 of FIG. 2A, the cross-section being taken along line A-A in FIG. 2A. As illustrated in FIG. 2B, guidewire 100 includes core wire 102, elongated body 104, support member 210, and atraumatic tip 105. Elongated body 104 may define an inner lumen 206 and support member 210 may define an inner lumen 208. Support member 210 may be disposed within inner lumen 206 of elongated body 104. A distal section 214 of core wire 102 may be connected to atraumatic tip 105. Distal section 214 of core wire 102 may be disposed within inner lumen 206 and inner lumen 208.

Distal section 110A and proximal section 110B may have a unitary body construction, e.g., may be formed as one body, such that a wall 107 of elongated body 104 is continuous along the entire length of elongated body 104, such that elongated body 104 is a single, seamless tubular body. A seamless elongated body 104 may, for example, be devoid of any seams (e.g., a seam formed from joining two separate tubular bodies together at an axial location along longitudinal axis 106), such that the seamless elongated body 104 is a unitary body, rather than multiple, discrete bodies that are separately formed and subsequently connected together. A seamless elongated body 104 may be easier to slide over another device, e.g., a guide member, compared to an elongated body formed from two or more longitudinal sections that are mechanically connected to each other because the seamless elongated body may define a smoother inner lumen. In contrast, joints between sections of an elongated body that are formed from two or more longitudinal sections may define surface protrusions or other irregularities along the inner lumen which may interfere with the passage of devices through the inner lumen. In addition, a seamless elongated body 104 may help distribute pushing and rotational forces along the length of guidewire 100. Thus, the seamless elongated body 104 may help contribute to the pushability of guidewire 100.

In some examples, a thickness of wall 107 of elongated body 104 is substantially constant along a length of elongated body 104. In other examples, the thickness of wall 107 varies along a length of elongated body 104. For example, the thickness of wall 107 may decrease toward distal end 104A (e.g., the thickness of wall 107 may decrease from proximal end 104B to distal end 104A of elongated body 104, or may decrease from a proximal end of distal section 110A to a distal end of distal section 110A). The thickness of linear wall 107 may linearly or non-linearly increase from distal end 104A. In some examples, the thickness of linear wall 107 may linearly or non-linearly decrease from proximal end 104B and/or from the distal end of distal section 110A. For example, the thickness of wall 107 may decrease from about 0.33 millimeters (mm) at the proximal end of elongated body 104 to about 0.0127 mm (about 0.0005 inches) at the distal end of elongated body 104. However, other wall thicknesses may be used in other examples, and may depend on the particular procedure for which guidewire 100 is used.

In some examples, elongated body 104 may define a same outer diameter along the length of elongated body 104 as the thickness of wall 107 varies along the length of elongated body 104. In such examples, an inner diameter of inner lumen 206 may vary along the length of elongated body 104, e.g., to maintain the same outer diameter. In some examples, inner lumen 206 may define a same inner diameter along the length of elongated body 104 as the thickness of wall 107 varies along the length of elongated body 104. In some examples, both the outer diameter of elongated body 104 and the inner diameter of inner lumen 206 may vary as the thickness of wall 107 varies along the length of elongated body 104.

In the example of FIG. 2B, openings 108 extend through the entire thickness of wall 107 (measured in a direction perpendicular to longitudinal axis 106 of guidewire 100, which may also be a longitudinal axis of elongated body 104). In other examples, openings 108 extend partially through wall 107. For example, openings 108 may extend from the outer surface of elongated body 104 towards but not reaching inner lumen 206 of elongated body 104. The depth of the partial opening 108 may be described as a percentage of the thickness of wall 107 or as a unit of length (e.g., millimeters). In some examples, the depth of a partial opening 108 may be about 20% to about 80% of the thickness of wall 107, such as about 50% to about 75% of the thickness of wall 107. In contrast, a through-opening 108 may extend through 100% of the thickness of wall 107.

In examples in which openings 108 include a plurality of partial openings, each partial opening 108 may have a substantially similar depth or at least two of the partial openings 108 may have different depths. For example, each of partial openings 108 may have the same depth as measured as a unit length. As another example, the unit length of the depths of the partial openings 108 may be different, but the depth as measured as a percentage of the thickness of wall 107 may be the same. If elongated body 104 is stretched during a manufacturing process, then a partial opening 108 at a more distal section of elongated body 104 may have a smaller depth than a more proximal opening 108; however, the percentage of thickness of the depth of the two openings 108 may be substantially the same (e.g., equal or within 5% of each other). In some examples in which openings 108 are partial openings, openings 108 extend from an outer surface of wall 107 toward inner lumen 206, where the outer surface may be the surface closest to an outer jacket or other outer layer or surface of guidewire 100.

In these examples, the inner surface of elongated body 104 defining inner lumen 206 may be relatively smooth, which may help facilitate the passage of medical devices through inner lumen 206. For example, a guide member may not catch on an opening 108 as it is being traversed through inner lumen 206 from a proximal end of guidewire 100 towards the distal end of guidewire 100. In other examples, openings 108 may extend from an inner surface of wall 107, which defines inner lumen 206, towards the outer surface. For example, an angular orientation of the openings relative to an axis that runs orthogonal to longitudinal axis 106 may be selected to minimize the possibility that a guide member will catch on the opening.

In some examples, opening 108 may be oblong shaped or define a concave portion. An oblong shaped opening may include, for example, an elongated rectangle, an elongated oval, ellipse, or another elongated polygonal shape (e.g., an elongated trapezoid, an elongated quadrilateral, an elongated pentagon, an elongated octagon, or the like). The depths, lengths, and/or widths of openings 108 may be at least partially defined by or may at least partially define the beam lengths, offset angles, pitches, and/or radii of curvature of openings 108.

Portions of elongated body 104 may define a density of openings 108, which may be the number of openings 108 per unit length of elongated body 104 (the length being measured in a direction along longitudinal axis 106). The density of openings 108 may be based on a length and/or width of each opening 108 and/or the beam length, the pitch, the angular offset angle, and/or the radii of curvature of openings 108. Longitudinally adjacent rows of openings 108 exhibiting reflectional symmetry, e.g., as illustrated in FIG. 2A, may increase the density of openings 108, e.g., by reducing an amount of space between the longitudinally adjacent rows.

In some examples, the density of openings 108 may be uniform along a length of elongated body 104. In some examples, the density of openings 108 may vary along the length of elongated body 104. For example, the density of openings 108 may increase in the distal direction, such that there are more openings 108 near distal end 104A of elongated body 104 than near proximal end 104. In these examples, for an elongated body 104 that is otherwise the same, distal section 110A of elongated body 104 may have a greater bending flexibility than proximal section 110B of elongated body 104. In another example, the density of openings 108 may decrease in the distal direction, such that there are fewer openings 108 near distal end 104A of elongated body 104 than near proximal end 104.

The density of openings 108 may increase as one or more of the beam lengths between openings 108, the pitches between openings 108, a length of each opening 108, and/or a width of each opening 108 decreases. In some examples, the density of openings 108 may increase as the radii of curvature of openings 108 increase. Conversely, the density of openings 108 may decrease as one or more of the beam lengths, the pitches, the lengths, and/or the widths of openings 108 increases and/or as the radii of curvature of openings 108 decrease.

The density of openings 108 on elongated body 104 may be about 4% to about 30% (e.g., such as about 5% to about 25%, about 11% to about 19%, or about 14%). A 4% density of openings 108 indicates that at a specific portion (e.g., region 204N) of elongated body 104, openings 108 encompass 4% of the surface area of the specific portion of elongated body 104 (e.g., 4% of the surface area of region 204N of elongated body 104). That is, about 4% to about 30% of elongated body 104 may be cut. The percentage of elongated body 104 that is cut may be, for example, a percentage of an area of an outer surface of elongated body 104.

Openings 108 may be formed on elongated body 104 using one or more techniques. In some examples, openings 108 may be etched, laser cut, or mechanically cut via a blade, router, abrasion disk, or the like into a tubular body or other material from which elongated body 104 is formed. In other examples, elongated body 104 may be formed by winding a ribbon of an elongated body material (e.g., PTFE) around a beading. As another example, elongated body 104 may be formed using an additive manufacturing process (also referred to as a three-dimensional printing technique in some examples). Openings 108 may then be defined during the additive manufacturing.

Support member 210 is configured to increase the structural integrity of guidewire 100 while allowing guidewire 100 to remain relatively flexible. For example, support member 210 may be configured to help guidewire 100 substantially maintain its cross-sectional shape or at least help prevent guidewire 100 from buckling or kinking as it is navigated through tortuous anatomy. In some examples, guidewire 100 may include another layer, such as a support layer, that adheres support member 210 to elongated body 104. Support member 210, together with elongated body 104, may help distribute both pushing and rotational forces along a length of guidewire 100, which may help prevent kinking of guidewire 100 upon rotation of guidewire 100 or help prevent buckling of guidewire 100 upon application of a pushing force to core wire 102. As a result, a clinician may apply pushing forces, rotational forces, or both, to proximal section 103B of guidewire 100, and such forces may cause distal section 103A of guidewire 100 to advance distally, rotate, or both, respectively. Support member 210 may define an inner lumen 208 configured to retain distal section 214 of core wire 102.

In the example of FIG. 2B, support member 210 extends along only a portion of a length of core wire 102. For example, a proximal end of support member 210 may be positioned distal to proximal end 104B of elongated body 104. The outer diameter of core wire 102 may reduce from proximal section 103B to atraumatic tip 105, e.g., to allow for placement of distal section 214 in inner lumen 206 of elongated body 104 and in inner lumen 208 of support member 210 without increasing the outer diameter of distal section 103A of guidewire 100.

In some examples, support member 210 includes a generally tubular braided structure, a coil member defining a plurality of turns, e.g., in the shape of a helix, or a combination of a braided structure and a coil member. Thus, although examples of the disclosure describe support member 210 as a coil, in some other examples, the catheter bodies described herein include a braided structure instead of a coil or a braided structure in addition to a coil. For example, a proximal section of support member 210 may include a braided structure and a distal section of structural support member 210 may include a coil member. Support member 210 can be made from any suitable material, such as, but not limited to, a metal (e.g., a nickel titanium alloy (Nitinol) or stainless steel), a polymer, a fiber, or any combination thereof.

Support member 210 may be coupled, adhered, or mechanically connected to at least a portion of an inner surface of elongated body 104, such as via a support layer. The support layer may be a thermoplastic material or a thermoset material, such as a thermoset polymer or a thermoset adhesive. In some cases, the material forming the support layer may have elastic properties, such that there may be a tendency for the support layer to return to a resting position. In some examples, the support layer is positioned between the entire length of support member 210 and elongated body 104. In other examples, the support layer is only positioned between a part of the length of support member 210 and elongated body 104.

Figure 3A:
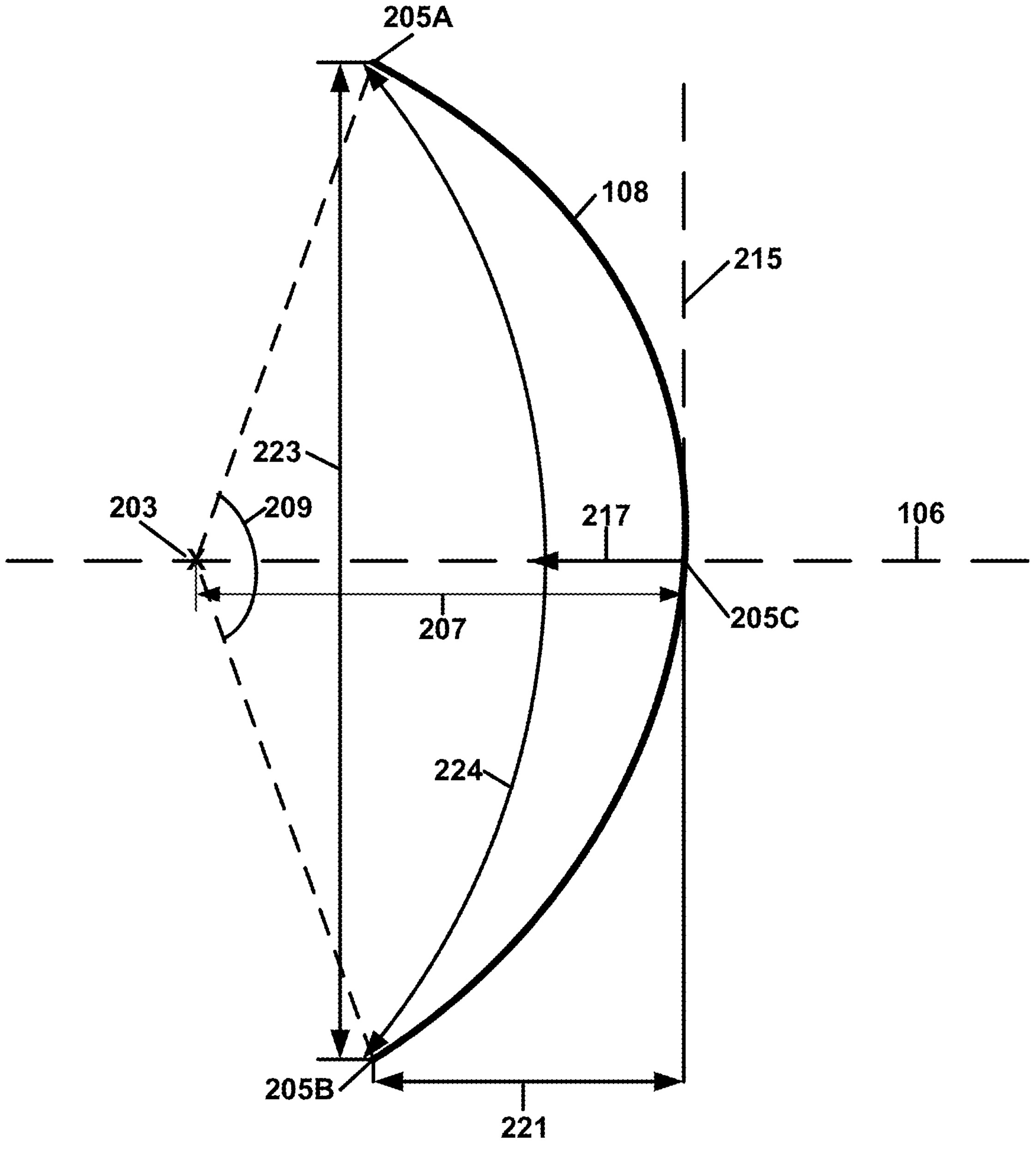
FIG. 3A is a conceptual diagram illustrating an example opening of the elongated body of FIG. 2A.

FIG. 3A is a conceptual diagram illustrating an example opening 108 of the elongated body 104 of FIG. 2A. As illustrated in FIG. 3A, opening 108 may have a non-linear shape from a first end 205A through a center 205C to a second end 205B. The non-linear shape may include an arc (e.g., a semicircular arc, a parabolic arc, an elliptical arc). For each opening 108, an arc length 224 (e.g., a distance along the length of the arc from first end 205A of to second end 205B) is greater than a chord length 223 (e.g., a linear distance between first end 205A and the second end 205B). Each arc may include a center point 203 defining a radial center of a circle, parabola, or ellipse defining the arc of opening 108.

For each opening 108, the arc may extend from first end 205A through center 205C to second end 205B. Center 205C defines a halfway point along the arc and may be equidistant (e.g., linearly, along the length of the arc) from both first end 205A and second end 205B. First end 205A and second end 205B may have a same longitudinal position relative to longitudinal axis 106 and center 205C may have a different longitudinal position than either first end 205A or second end 205B.

In some examples, each arc may define a concave portion extending from first end 205A through center 205C of the arc to second end 205B. The concave portion of the arc may face (i.e., in a direction 217 normal to a tangent axis 215 of center 205C of the arc) towards distal end 104A or proximal end 104B of elongated body 104 along longitudinal axis 106, e.g., such that a major axis 304 of the arc is orthogonal to longitudinal axis 106. Each arc may define a central angle 209 (e.g., relative to a center 203 of a circle, ellipse, or parabola defined by the arc) from first end 205A to second end 205B. The central angle may be up to about 180 degrees.

Each opening 108 defines an arc defining a radius of curvature 207. The radius of curvature 207 may be related to an axial span 221 (distance along axis 106) and a circumferential span (distance around axis 106) of the corresponding opening 108 (e.g., a chord length 223 of opening 108). The radius of curvature 207 for a given chord length 223 of opening 108 may define the axial span 221 of the opening 108, or vice versa. The radius of curvature 207 for a given axial span may define the chord length 223 of the opening 108, or vice versa. For example, a larger radius of curvature 207 for an opening 108 having a particular chord length 223 may define a smaller axial span 221 than an opening 108 of with an identical chord length 223 and a lower radius of curvature 207. The radius of curvature 207 of an opening 108 may influence a tensile strength and/or torque response of elongated body 104. The radii of curvature of openings 108 may allow for increase axial separation (e.g., along longitudinal axis 106) than linear openings orthogonal to longitudinal axis 106. Therefore, combining increased radii of curvature of openings 108 and decreased pitch between openings 108 may increase tensile strength of elongated body 104 while maintaining the bending stiffness and torque responsiveness of elongated body 104. By comparison, an elongated body having linear opening orthogonal to a longitudinal axis of the elongated body would define reduced bending stiffness as a result of increasing tensile strength, thereby reducing the pliability and bending radius of the elongated body, e.g., as compared to elongated body 104.

The radii of curvature 207 of openings 108 may vary between distal end 104A and proximal end 104B. As mentioned above, different portions of elongated body 104 may be configured to provide different functions, and the radii of curvature 207 may be varied to provide properties, such as varied bending flexibility or tensile strength, that are directed toward those particular functions.

In some examples, the variation of the radii of curvature 207 may be linear or non-linear. As one example, the radii of curvature 207 may change at a linear rate with respect to a distance along longitudinal axis 106. As another example, the radii of curvature 207 may change at a nonlinear rate (e.g., at an exponential rate, at a logarithmic rate) with respect to a distance along longitudinal axis 106. In some examples, the variation of the radii of curvature 207 may be continuous or discrete along elongated body 104. As one example, the radii of curvature 207 may continuously vary along the length of elongate body 107, such that each opening may have a different radius of curvature than adjacent openings along the longitudinal axis. As another example, the radii of curvature 207 of openings 108 may vary along specific portions of elongated body 104, the specific portions being separated by other portions of elongated body 104 including openings 108 defining uniform radii of curvature 207. In some examples, an opening 108 at proximal section 110B of elongated body 104 defines a smaller or larger radius of curvature than an opening 108 at distal section 110A of elongated body 104. Openings 108 defining a larger radii of curvature 207 may define larger angles 209 than openings 108 defining a smaller radii of curvature 207. Opening 108 defining a smaller radius of curvature 207 may reduce flexibility of elongated body 104 about the respective opening 108 relative to an opening 108 of a same chord length 223 defining a larger radius of curvature 207. Distal section 110A of elongated body 104 may define openings 108 defining larger radii of curvature than proximal section 110B of elongated body 104, e.g., to increase flexibility of distal section 110A relative to the proximal section. The radii of curvature 207 of openings 108 may be about 0.3 millimeters (mm) to about 3 mm (e.g., about 0.012 inches (in) to about 0.12 in).

Figure 3B:
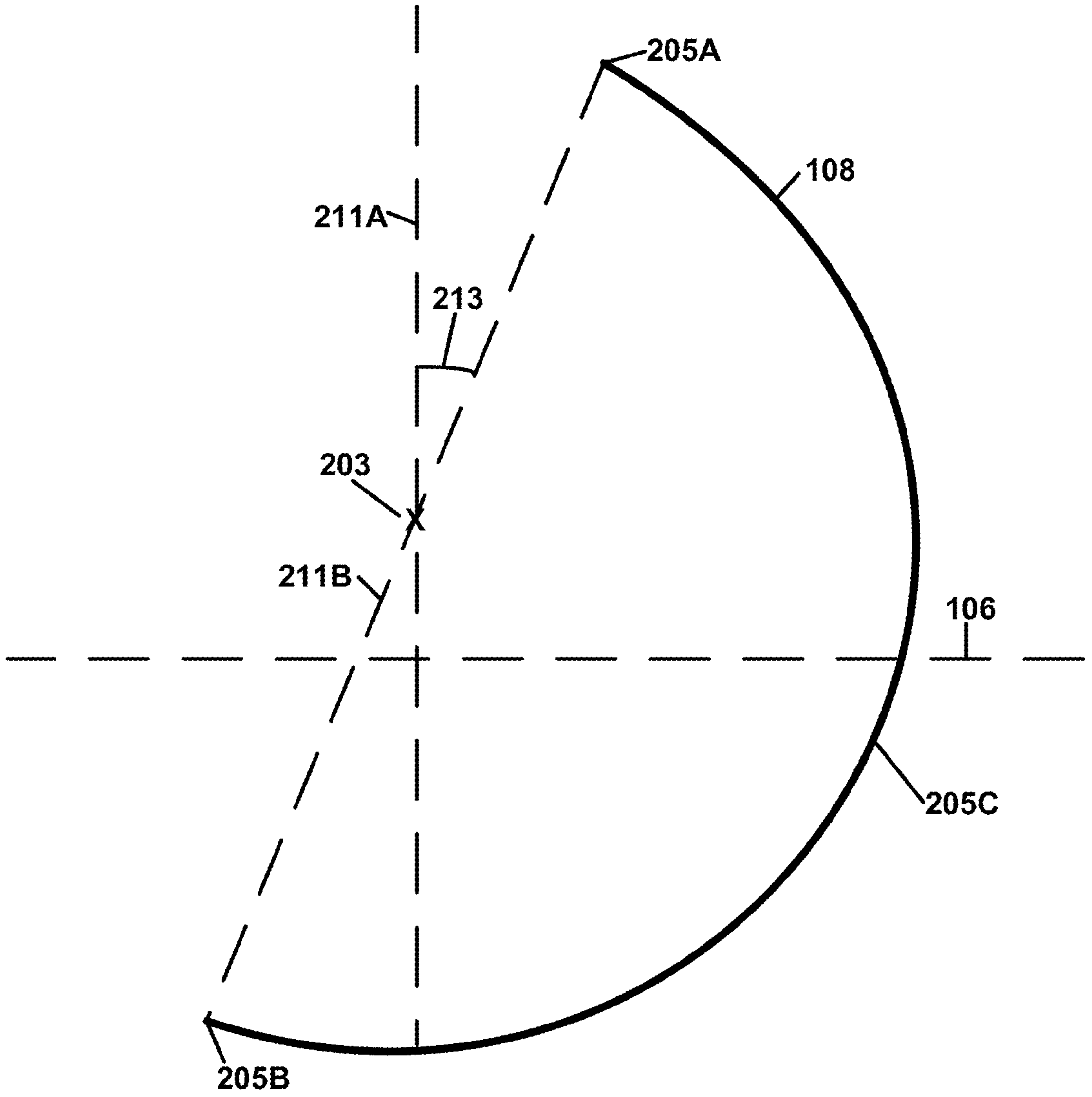
FIG. 3B is a conceptual diagram illustrating another example opening of the elongated body of FIG. 2A.

FIG. 3B is a conceptual diagram illustrating another example opening 108 of the elongated body 104 of FIG. 2A. Opening 108 may define a reference axis 211B extending linearly from first end 205A to second end 205B. Opening 108 may be offset from longitudinal axis 106, e.g., such that reference axis 211B is offset from reference axis 211A by angle 213. Reference axis 211A is orthogonal to longitudinal axis 106. Angle 213 may be up to about 90 degrees. Offsetting opening 108 from longitudinal axis 106, e.g., in the manner illustrated in FIG. 3B, may inhibit preferential bending of elongated body 104 along a specific plane in response to an external force on elongated body 104.

Figure 3C:
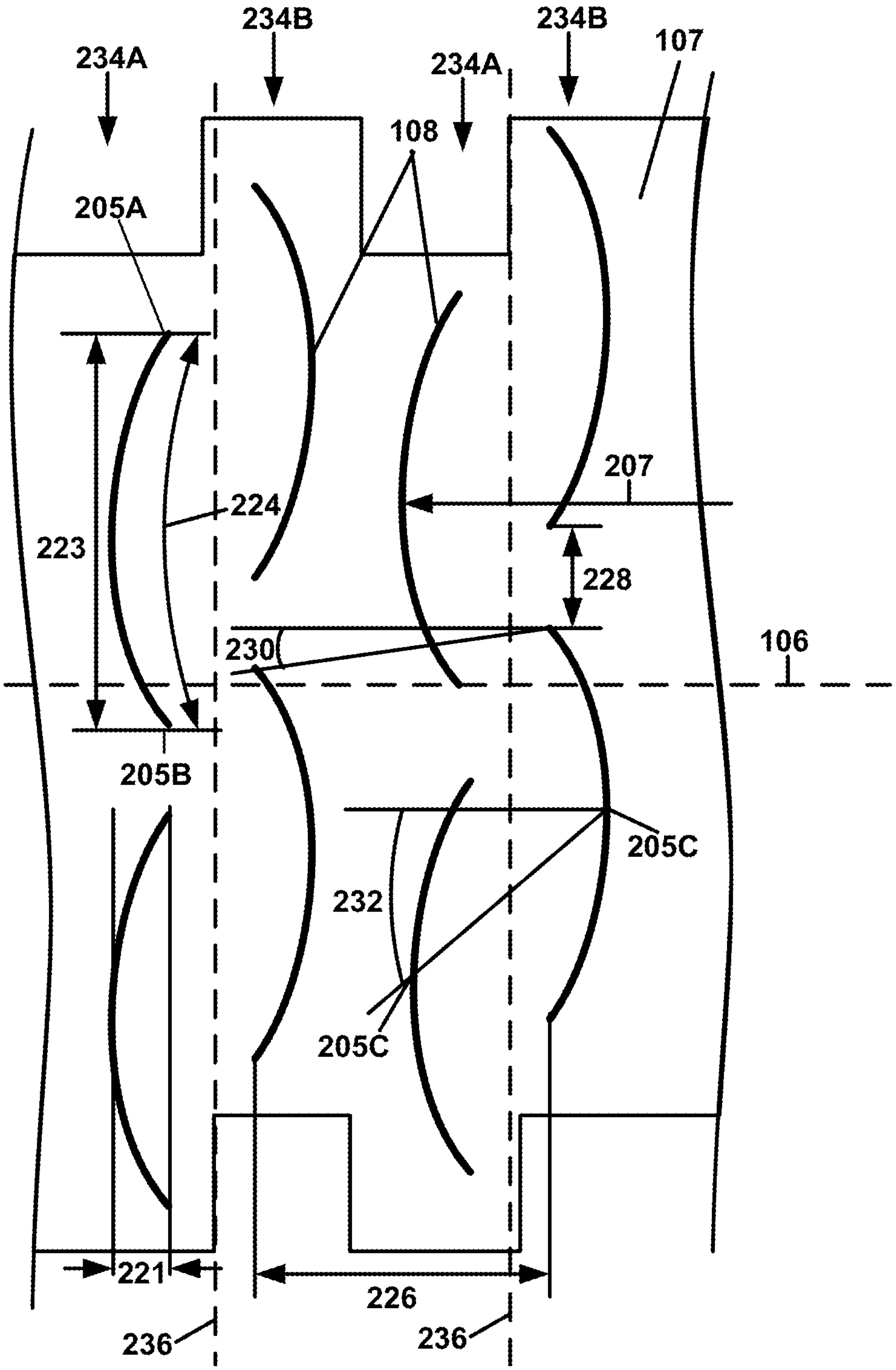
FIG. 3C is a conceptual diagram illustrating an example of the elongated body of FIG. 2A, the elongated body has been longitudinally cut and laid flat.

FIG. 3C is a conceptual diagram illustrating an example of the elongated body of FIG. 2A, the elongated body has been longitudinally cut and laid flat. Openings 108 may be arranged in circumferential rows 234A, B (collectively referred to herein as "circumferential rows 234", "rows 234"). around the circumference of elongated body 104. As illustrated in FIG. 3C, each row 234 of openings 108 may include two openings 108. In some examples, each row 234 of openings include one opening 108 or three or more openings 108. Circumferentially adjacent openings 108 of each row 234 are separated by an uncut portion of wall 107. As illustrated in FIG. 3C, each row 234 includes two uncut portions of wall 107. Opening 108 may be offset from longitudinal axis 106 in a clockwise direction, as illustrated in FIG. 3B (i.e., angle 213 extends from reference axis 211A to reference axis 211B in a clockwise direction. In some examples, opening 108 is offset from longitudinal axis 106 in a counterclockwise direction (i.e., angle 213 extends from reference axis 211A to reference axis 211B in a counterclockwise direction).

Each row 234 of openings 108 may define circumferentially adjacent openings 108 on a reference plane. The reference plane may be or normal to longitudinal axis 106. In some examples, the reference plane may be offset from a plane normal to longitudinal axis 106 by angle up to about 90 degrees (e.g., by about 45 degrees, by about 75 degrees, by about 80 degrees). Each row 234 of openings 108 may be longitudinally adjacent to one or more other rows of openings 108. For example, as illustrated in FIG. 3C, each circumferential row 234A is longitudinally adjacent to at least one circumferential row 234B and is longitudinally alternate to another circumferential row 234A. In some examples, each row of openings 108 may be directly adjacent to two other rows of openings 108 along longitudinal axis 106. For example, as illustrated in FIG. 3C, each circumferential row 234A is directly adjacent to at least one circumferential row 234B and is not directly adjacent to any other circumferential row 234A. As described in the disclosure, two rows of openings 108 that are longitudinally adjacent with no other row of openings 108 between the two rows are "directly adjacent."

Circumferentially adjacent openings 108 within each row are separated by an uncut portion of wall 107. Each uncut portion of wall 107 may be defined by a beam length 228. Beam length 228 corresponds to a length of the corresponding uncut portion of wall 107 around the circumference of elongated body 104. For example, first end 205A of one opening 108 is separated from second end 205B of a circumferentially adjacent opening 108 by beam length 228. Larger beam length 228 values may increase tension resistance of elongated body 104 relative to an elongated body 104 with identical openings 108 with smaller beam length 228 values. Smaller beam length 228 values may increase torque responsiveness of elongated body 104 relative to an elongated body 104 with identical openings 108 with larger beam length 228 values. The beam lengths 228 may vary along the length of elongated body 104, e.g., from distal end 104A to proximal end 104B. For example, as illustrated in FIG. 2A, the beam lengths 228 may increase from distal end 104A to proximal end 104B. The beam lengths 228 of openings 108 may include a minimum beam length value, e.g., such that a portion of elongated body 104 defines a minimum tensile strength that exceeds or is equal to a threshold minimum tensile strength required by the clinician.

Longitudinally alternate rows 234 of openings 108 may be separated by a pitch 226. For example, each circumferential row 234B of openings 108 is separated from a longitudinally alternate circumferential row 234B of openings 108 by pitch 226. Smaller pitches 226 may reduce the bending radius and/or the bending stiffness of elongated body 104 relative to another elongated body 104 with identical openings 108 separated by larger pitches 226. Larger pitches 226 may increase pushability of elongated body 104 relative to another elongate body 104 with identical openings 108 separated by smaller pitches 226. The pitch 226 may vary along the length of elongated body 104, e.g., from distal end 104A to proximal end 104B. For example, as illustrated in FIG. 2A, the pitches 226 of openings 108 increases from distal end 104A to proximal end 104B, e.g., to reduce the bending stiffness and bending radius of distal section 110A of elongated body 104 relative to proximal section 110B of elongated body 104.

The rows 234 of openings 108 may define repeating patterns 235 along elongated body 104. The repeating patterns 235 may define a helix or spiral along the longitudinal length of elongated body 104. For example, circumferential rows 234A of openings 108 may define a first helix or spiral along the longitudinal length of elongated body 104 and circumferential rows 234B of openings 108 may define a second helix or spiral along the longitudinal length of elongated body 104. Each helix or spiral may define a plurality of coils, each coil being defined by a separate circumferential row 234 of openings 108 The spacing between longitudinally adjacent coils of a helix or spiral may vary along the longitudinal length of elongated body 104, e.g., based on variations of pitch 226 between circumferential rows 234 of openings 108.

Each row 234 of openings 108 may be circumferentially offset from a corresponding row 234 of an adjacent repeating pattern 235 by an angular offset angle 230. For example, as illustrated in FIG. 3C, each circumferential row 234B is offset from a longitudinally adjacent circumferential row 234B by angular offset angle 230. The angular offset angle 230 may define a helical or rotational pitch of the repeating pattern 235, e.g., of the helix or spiral. Each repeating pattern 235 may include two or more rows 234 of openings 108. In some examples, a repeating pattern 235 may include a first circumferential row 234A of openings 108 and a second circumferential row 234B of openings 108, wherein the second circumferential row 234B of openings 108 is a mirror image of the first circumferential row 234A of openings 108 across a reference plane 236. The reference plane 236 may be orthogonal to longitudinal axis 106 or may be similar to or the same as reference axis 211A, as illustrated in FIG. 3B. In some examples, with respect to the first circumferential row 234A of openings 108, the corresponding circumferential row 234 of openings 108 of an adjacent repeating pattern 235 may be a longitudinally alternate circumferential row 234A of openings 108 of an adjacent repeating pattern 235. Each repeating pattern 235 may define a constant angular offset angle 230 or a varying angular offset angle 230. For example, as illustrated in FIG. 2A, the repeating pattern 235 of openings 108 defines angular offset angles 230 increasing from distal end 104A to proximal end 104B. Angular offset angles 230 may be about 4 degrees to about 14 degrees.

Each pattern 235 of the repeating pattern 235 may have different dimensions. One pattern 235 may include openings 108 defining different pitches 226, radii of curvature 207, beam lengths 228, and/or angular offset angles 230 than openings 108 of an adjacent pattern 235. For example, a first repeating pattern 235 includes openings 108 defining smaller pitches 226, smaller beam lengths 228, larger radii of curvature 207, and smaller angular offset angles 230 than openings 108 of a second repeating pattern 235 more proximal to the first repeating pattern 235, or vice versa. In some examples, the first repeating pattern 235 includes openings 108 with same or similar chord lengths 223, smaller arc lengths 224, and smaller axial spans 221 than openings 108 in the second repeating pattern 235. Elongated body 104 may define a same repeating pattern 235 along the length of elongated body 104 or may define two or more different repeating patterns 235 along the length of elongated body 104. Each repeating pattern 235 of the two or more different repeating patterns 235 may define a different helix or spiral.

Patterns 235 may define a spatial arrangement of openings 108 along (e.g., axially) and/or around (e.g., circumferentially) axis 106. Each pattern 235 may be internally symmetrical or asymmetrical. For example, openings 108 within each row 234 of opening 108 in a pattern 235 may be symmetrically arranged relative to longitudinal axis 106 to define radial symmetry. Openings 108 may define other types of symmetrical patterns 235 including, but not limited to, reflectional symmetry (e.g., mirrored openings 108), rotational, glide reflection, or helical symmetry. For example, as illustrated in FIG. 3C, openings 108 of each circumferential row illustrates radial symmetry. For example, as illustrated in FIG. 3C, openings 108 of first circumferential row 234A exhibit glide reflection symmetry and reflectional symmetry relative to openings 108 of second circumferential row 234B. In some examples, elongated body 104 may define a symmetrical opening along one portion of distal section 103A and an asymmetrical opening along a different portion of distal section 103A.

Pattern 235 may be repeating along the length of elongated body 104. The repeating patterns 235 may collectively define a helical or spiral arrangement of openings extending at least partially along elongated body 104. The same openings 108 of repeating patterns 235 may define a first helix or spiral having a first rotational pitch in one direction (e.g., in a clock-wise direction) and a second helix or spiral having a second rotational pitch in a second direction (e.g., in a counter-clockwise direction).

Each row 234 of openings 108 may be circumferentially offset a longitudinally adjacent row 234 of openings by circumferential offset angle 232. For example, each circumferential row 234A is circumferentially offset from a longitudinally adjacent circumferential 234B by circumferential offset angle 232. For example, a center 205C of opening 108 on a first circumferential row 234A is circumferentially offset from a corresponding opening 108 on a second circumferential row 234B longitudinally adjacent to the first circumferential row 234A. Longitudinally adjacent rows 234 may be circumferentially offset by a circumferential offset angle 232 of about 90 degrees plus half of the angular offset angle 230, e.g., to prevent preferential bending in any portion of elongated body 104 along any particular plane. For example, if the angular offset angle 230 between two longitudinally adjacent circumferential rows 234A is 14 degrees, the circumferential offset angle 232 between one of the two circumferential rows 234A and a circumferential row 234B between the two circumferential rows 234A is 97 degrees. In another example, if the angular offset angle 230 between two longitudinally adjacent circumferential rows 234B is 4 degrees, the circumferential offset angle 232 between one of the two circumferential rows 234B and a circumferential row 234A between the two circumferential rows 234B is 92 degrees. As the angular offset angle 230 between repeating patterns 235 of openings 108 varies along the length of elongated body 104 (e.g., increases from distal end 104A towards proximal end 104B), the circumferential offset angle 232 between longitudinally adjacent rows 234 of the rows 234 of openings 108 defining the repeating patterns 235 may vary accordingly.

In some examples, longitudinally adjacent rows 234 of openings 108 may be mirror images about a reference plane 236 orthogonal to longitudinal axis 106 or offset from longitudinal axis 106 by an angle (e.g., by angle 213). The mirroring of rows 234 of openings 108 may reduce the pitch 226 between longitudinally alternate rows 234 of openings 108 along longitudinal axis 106, thereby increasing a density of openings 108 along a set length of elongated body 104 as compared to a same set length on an identical elongated body 104 without any mirrored rows 234 of openings 108. The increased density in openings 108 increases flexibility of elongated body 104 relative to the identical elongated body 104 without any mirrored rows 234 of openings 108.

In some examples, the dimensions of openings 108 (e.g., the pitch, the radius of curvature, the beam length, the angular offset angle, the reflectional symmetry) may vary (e.g., linearly or non-linearly) between distal end 104A and proximal end 104B. Openings 108 may define a variation in the dimensions of openings 108 from distal end 104A to proximal end 104B. For example, the radius of curvature 207 of a first opening 108 is larger than the radius of curvature 207 of a second opening 108 proximal to the first opening 108. In some examples, the radii of curvature 207 of the first opening 108 and the second opening 108 are larger than the radius of curvature 207 of a third opening 108 proximal to the second opening 108.

A row 234 of openings 108 may be separated from a first longitudinally adjacent row 234 of openings 108 by a first pitch and from another longitudinally adjacent row 234 of openings 108 by a second pitch different from the first pitch. For example, one row 234A of openings 108 may be separated from a longitudinally adjacent and proximal row 234B of openings 108 by the first pitch and from a longitudinally adjacent and distal row 234B of openings 108 by the second pitch. In such examples, pitch 226 between longitudinally alternating rows 234 may be a sum of the first pitch and the second pitch. longitudinally adjacent rows 234 may be separated by a distance alternating between a first pitch and a second pitch. The non-uniform pitches between longitudinally adjacent rows 234 may increase tensile stiffness of elongated body 104 without reducing torque responsiveness of elongated body 104.

Within each region 204, the first pitch may define a uniform longitudinal distance and the second pitch may define another uniform longitudinal distance. For example, within an example region 204, the first pitch may be about 0.15 mm (e.g., about 0.006 in) and the second pitch may be about 0.20 mm (e.g., about 0.008 in). In some examples, within each region 204, the first pitch and the second pitch may define variable longitudinal distances. The first pitch and the second pitch may increase or decrease from distal end 104A to proximal end 104B. For example the first pitch between rows 234 at or around distal end 104A is less than the first pitch between rows 234 at or around proximal end 104B, or vice versa.

Figure 3D:
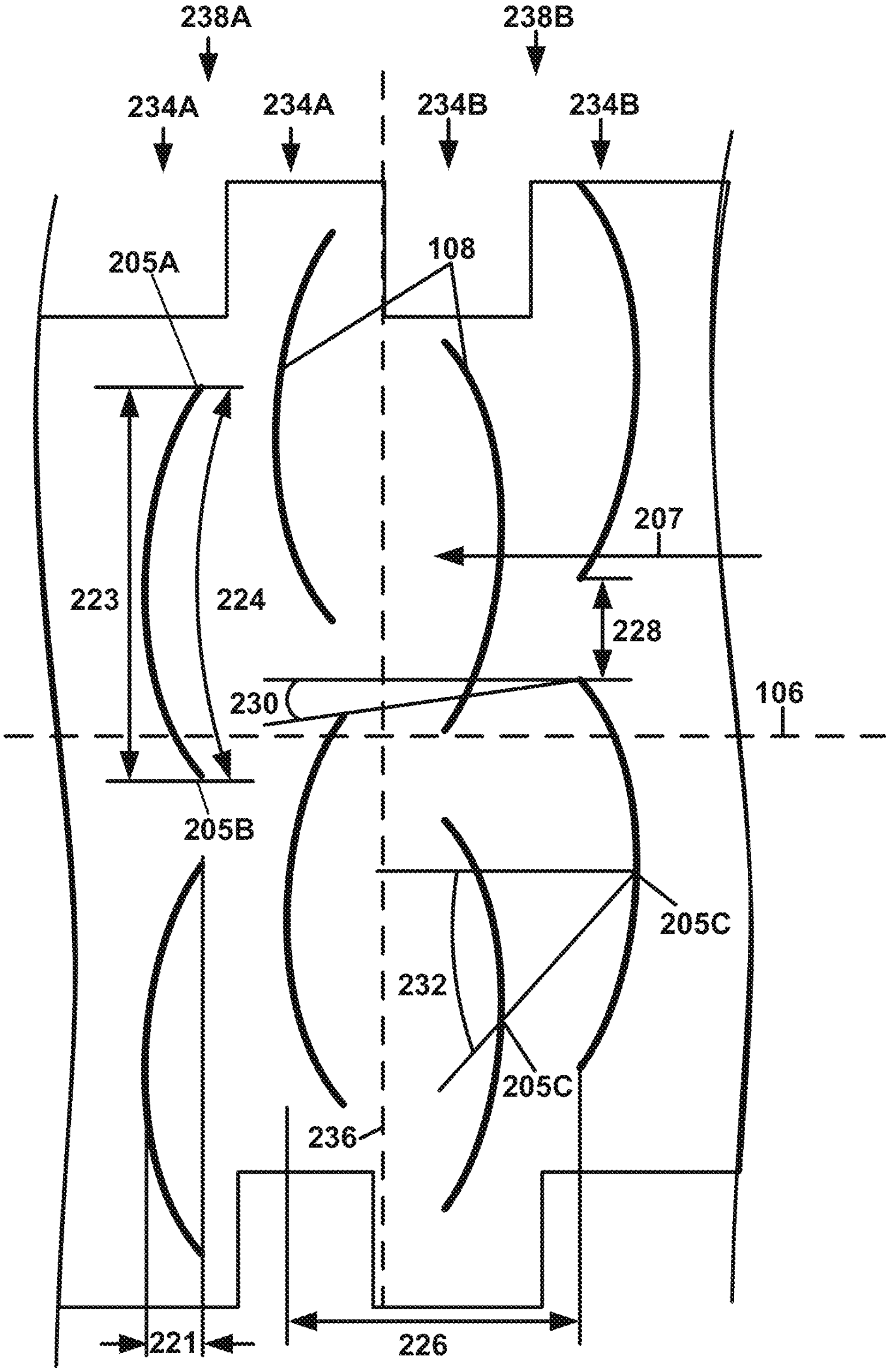
FIG. 3D is a conceptual diagram illustrating another example of the elongated body of FIG. 2A, the elongated body has been longitudinally cut and laid flat.

FIG. 3D is a conceptual diagram illustrating another example of the elongated body of FIG. 2A, the elongated body has been longitudinally cut and laid flat. As illustrated in FIG. 3D, two or more longitudinally adjacent rows 234 of openings 108 may define a group 238A, 238B (collectively referred to herein as "groups 238") of rows 234. The rows 234 within each group 238 may be of a same type. For example, group 238A only includes circumferential rows 234A and group 238B only includes circumferential rows 234B. One group 238A may be a mirror image of another group 238B across a reference plane 236. Mirroring groups 238 of rows 234 may increase density of openings 108 along a set portion of elongated body 104 relative to another elongated body 104 without mirrored groups 238 of rows 234.

Figure 4:
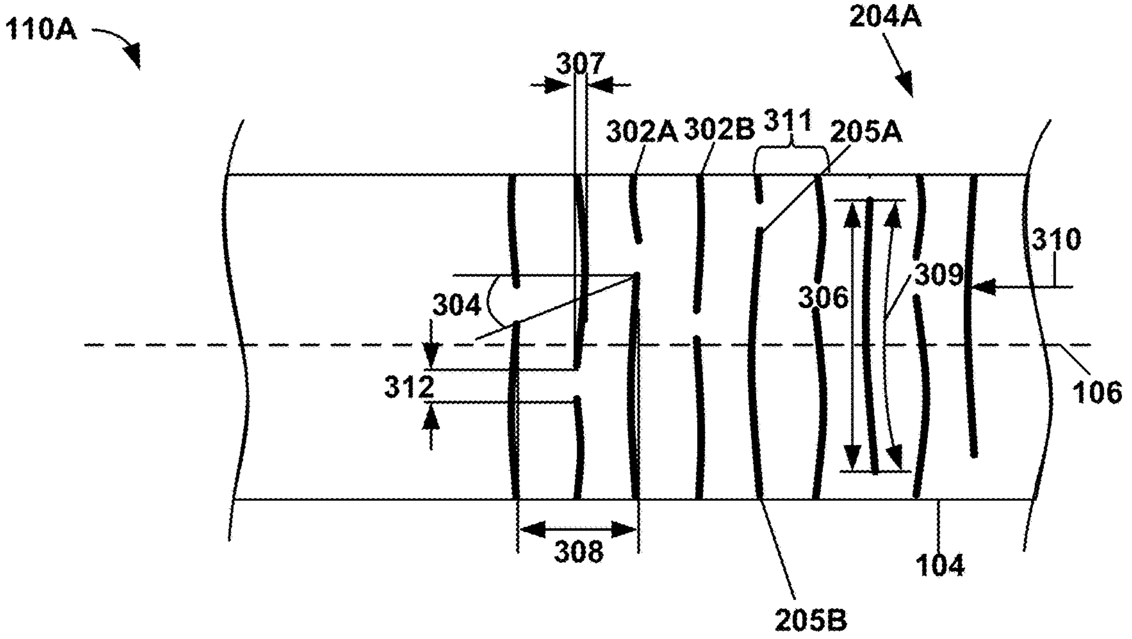
FIG. 4 is a conceptual diagram illustrating a distal section of the elongated body of FIG. 1.
Figure 5:
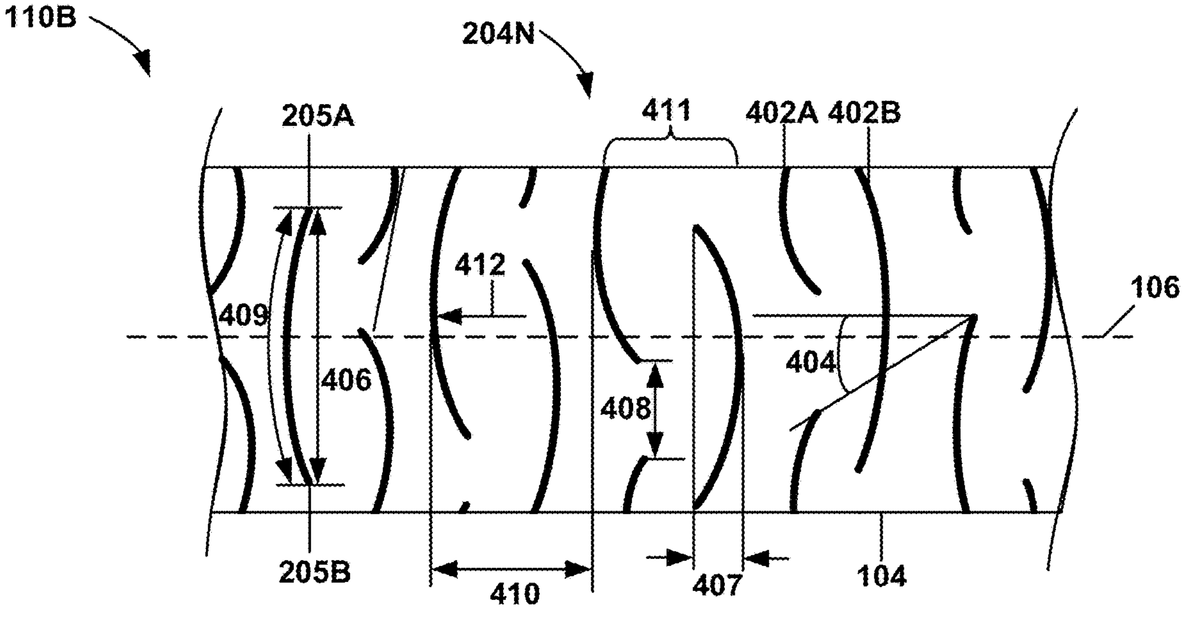
FIG. 5 is a conceptual diagram illustrating a proximal section of the elongated body of FIG. 1.

FIG. 4 is a conceptual diagram illustrating a distal section 110A of elongated body 104 of FIG. 1. FIG. 5 is a conceptual diagram illustrating a proximal section 110B of elongated body 104 of FIG. 1. As illustrated in FIGS. 4 and 5, the openings define both varying radii of curvature and reflectional symmetry. In some examples, openings on elongated body 104 may define either the varying radii of curvature or the reflectional symmetry. In addition, while the openings illustrated in FIGS. 4 and 5 define an arc, the examples described below may include openings defining other shapes.

As illustrated in FIG. 4. openings 108 may include a first group of openings 108 ("openings 302A") and a second group of openings 108 ("openings 302B"). Similarly, as illustrated in FIG. 5, openings 108 may include first group of openings ("openings 402A") and a second group of openings ("openings 402B"). In some examples, openings 302B may have different dimensions than openings 302A and openings 402B may have different dimensions 402A. In some examples, openings 302B may be mirror images of openings 302A (e.g., about a reference plane normal to longitudinal axis 106). In some examples, openings 402B may be mirror images of openings 402A (e.g., about a reference plane normal to longitudinal axis 106). In some examples, openings 302A may be the same as openings 302B and/or openings 402A may be the same as openings 402B.

In some examples, openings 302A, 302B, 402A, and 402B may each define a different repeating pattern 235 of openings. In some examples, one or more rows of openings 302A and one or more rows of openings 302B may define a first repeating pattern 235 and one or more rows of openings 402A and one or more rows of openings 402B may define a second repeating pattern 235. In some examples, rows of openings 302A and rows of openings 302B may define the repeating pattern 235 and openings 402A, 402B may define the same repeating pattern 235, e.g., with different dimensions (e.g., different lengths, widths, depths, beam lengths, pitches, angular offset angles, radii of curvature).

As illustrated in FIG. 4, each of openings 302A, 302B (collectively referred to as "openings 302") define an arc. For each of openings 302, the arc may extend from a first end, through a center, and terminate in a second end. For each of openings 302, the first end and the second end may have a first longitudinal position relative to longitudinal axis 106 and may have a different longitudinal position than the center. Each arc defined by openings 302 defines a concave portion extending towards a distal end of elongated body 104 (distal end 104A of FIG. 1, 2A, or 2B) or towards a proximal end of elongated body 104 (proximal end 104B of FIG. 1, 2A, or 2B). For example, as illustrated in FIG. 4, openings 302A define concave portions extending towards proximal end 104B and openings 304B define concave portions extending towards distal end 104A. Each of openings 304B may be a mirror image of one or openings 304A.

Openings 302A and openings 302B may define rows of like openings, each circumferential row extending around a perimeter of elongated body 104. For example, each row of like openings may include entirely of openings 302A or openings 302B. Rows of openings 302 may be directly adjacent to each other, e.g., wherein the rows of openings 302 are not separated by a third row of openings 302 along longitudinal axis 106. In some examples, rows of openings 302 may be longitudinally alternating (also referred to herein as "longitudinally alternate rows"), e.g., wherein the rows of openings 302 are separated by a third row of openings 302 along longitudinal axis 106.

In some examples, longitudinally adjacent rows of like openings (e.g., of openings 302A) may be separated by two or more rows of different openings (e.g., openings 302B). For example, each row of openings 302B may be directly adjacent to one row of openings 302A and one row of openings 302B. In such examples, each row of openings 302B may be a mirror image of the directly adjacent row of openings 302A. Within each row of openings 302, openings 302 are disposed around a perimeter of elongated body 104. Openings 302 may be symmetrically or asymmetrically disposed around the perimeter. Each row may include a plurality of openings 302, e.g., two or more openings 302.

Longitudinally adjacent rows of openings 302 may be circumferentially offset from each other. For example, each opening 302 in each row of openings 302 is circumferentially offset from a longitudinally adjacent opening 302 in a longitudinally adjacent row of openings 302. Alternatively, longitudinally adjacent rows of openings 302 may be offset from each other around the perimeter of elongated body 104. The offset of the adjacent rows of openings 302 may prevent preferential bending of elongated body 104 along a particular plane. The center of each opening 302 may be circumferentially offset from the centers of longitudinally adjacent openings 302 by a circumferential offset angle of 90 degrees plus half of the angular offset angle between repeating patterns 235 of openings 302. For example, the angular offset angle between repeating patterns 235 of openings 302 is about 4 degrees to about 14 degrees and the circumferential offset angle of longitudinally adjacent rows of openings 302 is about 92 degrees to about 97 degrees.

Distal section 110A of elongated body 104 may include one or more of regions 204, e.g., region 204A. Regions 204 may be configured with openings 302 or rows of openings 302 having different parameters, such that different regions 204 may have different characteristics, such as bending flexibility. For example, a particular region 204 may have characteristics suited for a particular function of the particular region 204 at the location on elongated body 104, or may provide a transition between adjacent regions 204. Each of regions 204 may include one or more rows of openings 302A and/or one or more rows of openings 302B. In some examples, as illustrated in FIG. 4, region 204A include a plurality of rows of openings 302A and a plurality of rows of openings 302B. In some examples, region 204A may include a single row of openings 302A and a single row of openings 302B. In some examples, region 204A may include two or more rows of openings 302A and a longitudinally adjacent region (e.g., region 204B) may include two or more rows of openings 302B. In such examples, region 204B may be a mirror image of region 204A.

Each of openings 302 may be defined by a length 306, a axial span 307, and a depth (not labelled). Axial span 307 of each opening 302 may be measured along longitudinal axis 106, e.g., from a center of each opening 302 to the ends of the opening 302. Length 306 may be measured along an axis normal to longitudinal axis 106. Lengths 306 and axial spans 307 may vary along the length of distal section 110A and/or within each of regions 204. In other examples, lengths 306 and axial spans 307 may be the same within each of regions 204.

Length 306 may be measured from a first end of each opening 302 to a second end of the opening 302. Length 306 may be a linear length (also referred to as "chord length") from the first end to the second end or an arc length along opening 302 from the first end to the second end. At a distalmost portion of distal section 110A, each opening 302 may be substantially straight (e.g., such that the chord length and the arc length of opening 302 are the same). Axial spans 307 of each opening 302 may be determined based on length 306 and radius of curvature 310 of each opening 302. The depth may be measured from an outer radial limit of opening 302 to an inner radial limit of opening 302. For example, for an opening that extends through wall 107, a depth may be a distance between an outer surface of wall 107 and an inner surface of wall 107. As another example, for an opening that does not extend through wall 107, a depth may be a total distance between the outer surface of wall 107 and the inner surface of wall 107 that does not include a material of wall 107.

Within each row of openings 302, circumferentially adjacent openings 302 are separated by beam length 312. Beam length 312 may be an uncut length of elongated body 104 between circumferentially adjacent openings 302. For example, a first end of one of openings 302 is separated from a second end of a circumferentially adjacent opening 302 by beam length 312. Beam lengths 312 may vary along elongated body 104. Increasing beam lengths 312 may increase tensile strength, torque responsiveness, and pushability of elongated body 104. Decreasing beam lengths 312 may increase flexibility of elongated body 104. Beam lengths 312 may increase from a distal end of distal section 110A (e.g., distal end 104A) towards a proximal end of distal section 110A, e.g., to increase flexibility of distal section 110A. In some examples, a distalmost section of elongated body 104 may include row(s) of openings 302 defining a larger beam length 312 than a more proximal row of openings 302 in distal section 110A, e.g., to increase stiffness of a distalmost section of elongated body 104. In some examples, openings 302 in each of regions 204 may define a same beam length 312. In some examples, mirroring rows of openings 302 may define a same beam length 312.

Longitudinally alternating rows of openings 302 may be separated by pitch 308. Pitch 308 may be measured as a longitudinal distance along longitudinal axis 106. Pitch 308 may be measured with respect to a same location (e.g., the center, the first end, the second end) on the corresponding openings 302. Pitches 308 may vary along the length of elongated body 104, e.g., to increase stiffness or flexibility at particular sections of elongated body 104. Larger pitches 308 may increase bending stiffness and/or the bending radius of elongated body 104, thereby increasing pushability along the length of guidewire 100. Smaller pitches 308 may reduce bending stiffness and/or bending radius of elongated body 104, thereby increasing the flexibility of a portion of elongate body 104. The variation in pitches 308 may be linear or non-linear.

Pitches 308 may increase from the distal end of distal section 110A towards a proximal end of distal section 110A, e.g., to increase the flexibility along distal section 110A. In some examples, pitches 308 of rows of openings 302 at a distalmost section of distal section 110A may be greater than pitches 308 between more proximal rows of openings 302 in distal section 110A, e.g., to increase the stiffness of a distalmost section of distal section 110A of elongated body 104. In some examples, rows of openings 302 in each of regions 204 may be separated by a same pitch 308 and rows of openings 302 in different regions 204 may be separated by different pitches 308.

As illustrated in FIG. 4, each pair of rows of openings 302A and 302B may form a pattern 311 representing a repeating unit of an overall pattern of elongated body 104. Within each pattern 311, openings 302A and 302B are mirror images of each other and are circumferentially offset by an angle of up to 90 degrees. A plurality of patterns 311 may define a helix or spiral along the length of elongated body 104. In some examples patterns 311 may define a first helix or spiral in one direction (e.g., in a clockwise direction) and a second helix or spiral in another direction (e.g., in a counterclockwise direction). The helix or spiral may be defined by a helical or rotational pitch. The helical pitch may be constant along the length of elongated body 104 or may vary from the distal end to the proximal end of distal section 110A. In some examples, the helical pitch may increase from the distal end to the proximal end of distal section 110A.

Longitudinally adjacent patterns 311 may be offset by angular offset angle 304. Two corresponding openings 302 (e.g., two corresponding openings 302A, as illustrated in FIG. 4) of the two longitudinally adjacent patterns 311 may define angular offset angle 304. For example, the circumferential offset between the centers, the first ends, and/or the second ends of the two corresponding openings 302 may define angular offset angle 304. Angular offset angle 304 may be up to 15 degrees, e.g., up to 10 degrees. In some examples, offset angle 304 is about 4 degrees to about 14 degrees. Angular offset angle 304 may vary (e.g., linearly or non-linearly) along the length of distal section 110A. For example, angular offset angle 304 may decrease from the distal end to the proximal end of distal section 110A. In some examples, angular offset angle 304 may be about 7.75 degrees to about 10 degrees.

Angular offset angle 304 may control the circumferential offset angle between longitudinally adjacent rows of openings 302 (e.g., within a same pattern 311 defining angular offset angle 304). The circumferential offset angle may be about 90 degrees plus half of angular offset angle 304. For example, is angular offset angle 304 is 14 degrees, the circumferential offset angle between longitudinal adjacent rows of openings 302 of pattern 311 defining angular offset angle 304 is 97 degrees.

Each of openings 302 may define a radius of curvature 310. A larger radius of curvature 310 reduces the curvature of opening 302, which may maintain or improve torque responsiveness of elongated body 104 compared to an elongated body that includes openings with a lower radius of curvature. A lower radius of curvature 310 increases the curvature of opening 302, which may increase tensile strength of elongated body 104 compared to an elongated body that includes openings with a lower radius of curvature. In some examples openings 302 may define varying radii of curvature 310 along elongated body 104, e.g., from the distal end to the proximal end of distal section 110A. The variation may be linear or non-linear. In some examples, radii of curvature 310 may decrease from the distal end to the proximal end of distal section 110A, e.g., to increase tensile strength along the length of distal section 110A while maintaining the torque responsiveness of elongated body 104.

Mirroring rows of openings 302 may include openings 302 having the same dimensions (e.g., the same lengths 306, axial spans 307, beam lengths 408, pitches 410, radii of curvature 310, and/or depths). For example, as illustrated in FIG. 3, each row of openings 302A may have openings 302A having same lengths 306 and axial spans 307 as openings 302B of a longitudinally adjacent row of openings 302B. Longitudinally adjacent rows of openings 302 and/or longitudinally adjacent regions 204 may define different dimensions.

FIG. 5 illustrates an example proximal section 110B of elongated body 104. Proximal section 110B includes a plurality of openings 402A, 402B (collectively referred to as "openings 402"). Openings 402 may be similar to openings 302 of FIG. 4 with different dimensions. In some examples, each of openings 402B is a mirror image of one of openings 402A. Openings 402A may be arranged into circumferential rows of openings 402A and openings 402B may be arranged into circumferential rows of openings 402B. Each row of openings 402B may be circumferentially offset from a longitudinally adjacent row of openings 402A by an angle. For example, openings 402B may be circumferentially offset from longitudinally adjacent openings 402A by the angle. The angle may be up to 90 degrees, e.g., the angle may be 45 degrees. As illustrated in FIG. 5, openings 402A, 402B (collectively referred to as "openings 402") may define dimensions (e.g., lengths, widths, depths, beam lengths, pitches, angular offset angles, circumferential offset angles, radii of curvature) having different values than openings 302 of FIG. 4.

Proximal section 110B may include one or more of regions 204 (e.g., region 204N), each region 204 include one or more rows of openings 402A and/or one or more rows of openings 402B. Rows of openings 402A and of openings 402B may define pattern 411. For example, each of pattern 411 may include a single row of openings 402A and a single row of openings 402B. In other examples, pattern 411 may include two or more of rows of openings 402A and/or of rows of openings 402B. Pattern 411 may be a same pattern or a different pattern as pattern 311 of FIG. 4. A plurality of patterns 411 may define a helix or spiral extending along proximal section 110B. The helix or spiral formed by patterns 411 may be a part of a helix or spiral formed by pattern 311 or may be a separate helix or spiral.

Each of openings 402 may define a length, a axial span 407, and a depth. Lengths, axial spans 407, and the depths of openings 402 may be similar to lengths 306, axial spans 307, and the depths of openings 302 but with different values. For example, lengths and axial spans 407 may be measured in a same manner as lengths 306 and axial spans 307, respectively. Lengths and axial spans 407 may vary along proximal section 110B. For example, lengths may increase from a distal end of proximal section 110B to a proximal end of proximal section 110B (e.g., proximal end 104B) and axial spans 407 may increase from the distal end of proximal section 110B to the proximal end of proximal section 110B. Lengths of each of openings 402 may include an arc length 406 and a chord length 409, e.g., as discussed above.

Circumferentially adjacent openings 402 may be separated by a beam length 408. Beam length 408 represents a circumferential length of an uncut portion of elongated body 108 between openings 402 and may be measured from a first end of one opening 402 to a second end of a circumferentially adjacent opening 402. A portion of elongated body 104 with openings 402 defining larger beam lengths 408 may exhibit increased tensile resistance and torque responsiveness relative to another portion of elongated body 104 with a lower beam length 408.

Beam lengths 408 may vary along a length of proximal section 110B of elongated body 104. In some examples, beam lengths 408 may increase from a distal end of proximal section 110B to a proximal end of proximal section 110B. In some examples, longitudinally adjacent or alternating rows of openings 402 may define different beam lengths 408. In some examples, row of openings 402 within a same region 204 may define a same beam length 408 and different regions 204 may define different beam lengths 408.

Pitch 410 may be a longitudinal distance between longitudinally alternating rows of openings 402. Pitch 410 may be measured between same points on openings 402 of alternate rows of openings 402 (e.g., between centers of two openings 402, between first ends of two openings 402, between second ends of two openings 402). Pitch 402 may vary along proximal section 110B of elongated body 104. For example, pitch 402 may increase from a distal end of proximal section 110B to the proximal end of proximal section 110B. The increase in pitch 402 along proximal section 110B may increase bending stiffness of elongated body 104 along proximal section 110B. In some examples, pitch 402 may linearly or non-linearly vary along proximal section 110B.

Longitudinally adjacent patterns 411 may be offset by angular offset angle 404. Two corresponding openings 402 (e.g., two corresponding openings 402A, as illustrated in FIG. 5) of the two longitudinally adjacent patterns 411 may define angular offset angle 404. For example, the circumferential offset between the centers, the first ends, and/or the second ends of the two corresponding openings 402 may define angular offset angle 404. Angular Offset angle 304 may vary (e.g., linearly or non-linearly) along the length of elongated body 104. For example, angular offset angle 304 may decrease from a distal end of proximal section 110B to a proximal end of proximal section 110B. In some examples, angular offset angle 404 may be about 4 degrees to about 7 degrees. Angular offset angle 404 may control the circumferential offset angle of longitudinally adjacent rows of openings 402 within each pattern 411, e.g., as described previously herein.

Each of openings 402 may define a radius of curvature 412. Radii of curvature 412 may be greater than radii of curvature 310, e.g., to increase tensile strength of proximal section 110B of elongated body 104. Radii of curvature 412 may vary along proximal section 110B. In some examples, radii of curvature 412 increases from the distal end of proximal section 110B to the proximal end of proximal section 110B.

In some examples, as illustrated in FIGS. 4 and 5, elongated body 104 is separated into distal section 110A and proximal section 110B, each section having openings 108 defining different parameters (e.g., different lengths, widths, pitches, radii of curvature, beam lengths, angular offset angles, circumferential offset angles, or the like). In other examples, elongated body 104 is separated into three or more sections along longitudinal axis 106 (e.g., 10 sections, 13 sections, 20 sections). Each section of elongated body 104 may include openings 108 defining different parameter values from one or more other sections of elongated body 104. The sections of elongated body 104 may be formed from a single continuous elongated member.

Across the sections of elongated body 104 (e.g., from distal end 104A to proximal end 104B). openings 108 (e.g., openings 302, 402) within the sections may define lengths having arc lengths (e.g., arc lengths 309, 409) of about 0.300 mm to about 0.500 mm (e.g., about 0.0118 in to about 0.0197 in) and chord lengths (e.g., cord lengths 306, 406) of about 0.300 mm to about 0.5 mm (e.g., about 0.0118 in to about 0.0197 in). Openings 108 may define beam lengths (e.g., beam lengths 312, 408) of about 0.0600 mm to about 0.200 mm (e.g., about 0.0023 in to about 0.0079 in). Openings 108 may define pitches (e.g., pitch 308, 410) of about 0.12 mm to about 2.54 mm (e.g., about 0.0048 in to about 0.0100 in). Openings 108 may define angular offset angles (e.g., angular offset angles 304, 404) of about 4 degrees to about 14 degrees. Openings 108 may define radii of curvature (e.g., radii of curvature 310, 412) of about 0.50 mm to about 3.30 mm (e.g., about 0.0196 in to about 0.130 in).

Figure 6A:
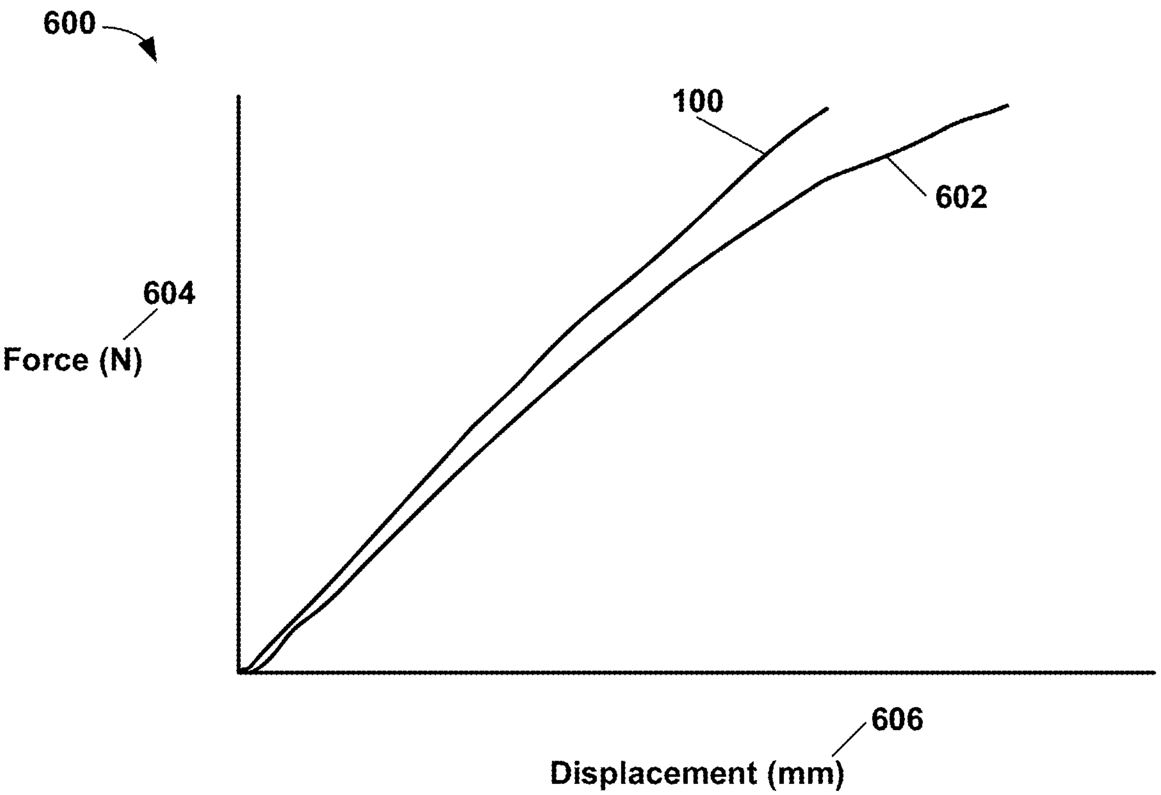
FIG. 6A is a graph illustrating example bending stiffness of the example guidewire of FIG. 1.

FIG. 6A is a graph 600 illustrating example bending stiffness of the example guidewire 100 of FIG. 1. Graph 600 illustrates bending forces 604 experienced by guidewire 100 and by a comparable guidewire 602 in response to displacement 606 of guidewire 100. The elongated body of guidewire 602 may define linear openings extending along planes orthogonal to the longitudinal axis of the elongated body. The elongated body of guidewire 602 may define varying parameters of openings (e.g., pitches between openings, beam lengths between openings, circumferential offset angles) along the length of the elongated body.

A greater amount of bending force 604 experienced by a guidewire in response to a particular amount of displacement 606 corresponds to increased bending stiffness of the guidewire. Displacement 606 defines an amount of bending away from a longitudinal axis of guidewires 100, 602 (e.g., longitudinal axis 106 of guidewire 100). For each of guidewire 100, 602, a larger displacement 506 represents greater bending of guidewire 100, 602 away from the longitudinal axis of each respective guidewire. Guidewire 602 may include an elongated body having the same or similar dimensions (e.g., length, thickness, outer diameter of the elongated body) as elongated body 104 of guidewire 100.

As illustrated in FIG. 6A, guidewire 606 may experience a similar force 504 in response to a same level of displacement 606 as guidewire 100. In some examples, guidewire 100 experiences relatively increased or relatively decreases forces 604 in response to the same level of displacement 606. The level of force experienced by guidewire 100 in response to a particular amount of displacement 606 may be dependent on the radii of curvature of openings 108 of elongated body 104 of guidewire 100 and/or the density of openings 108 along a portion of elongated body 104 (e.g., the pitch and/or beam length between openings 108). For example, an increased density of openings 108 reduces the amount of force experienced by guidewire 100 for a given amount of displacement 606, thereby reducing the bending stiffness of guidewire 100. In some examples, the varying parameters of openings 108 described herein may cause a significant increase in tensile stiffness of guidewire 100 in exchange for a marginal increase in bending stiffness of guidewire 100.

Figure 6B:
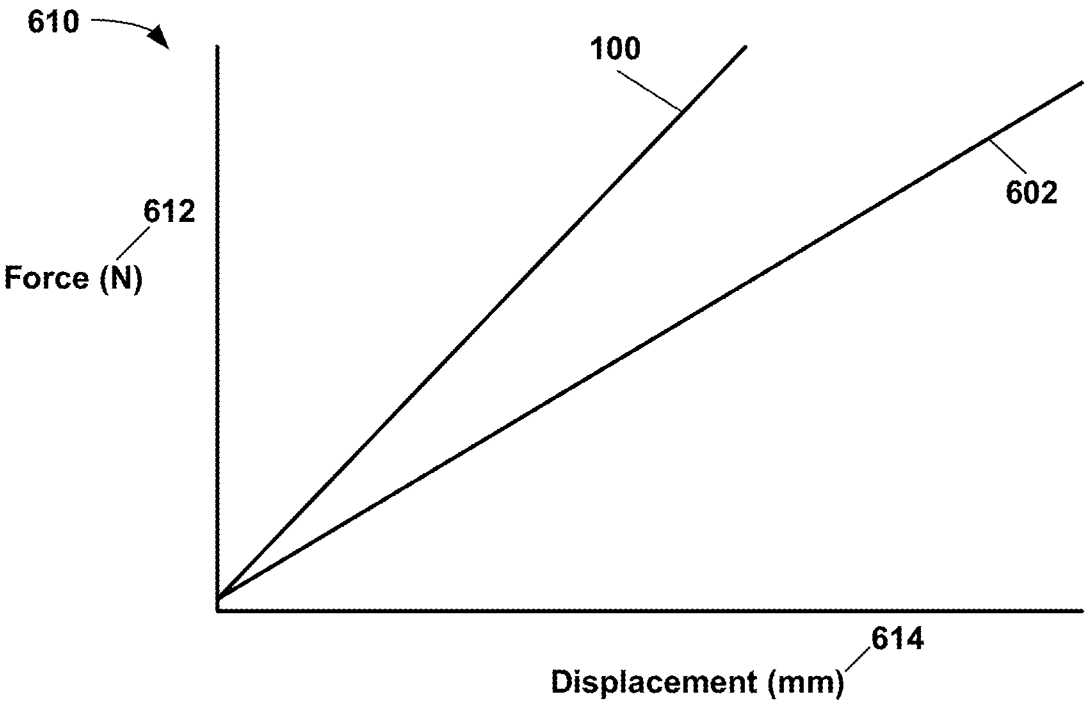
FIG. 6B is a graph illustrating example tensile stiffness of the example guidewire of FIG. 1.

FIG. 6B is a graph 610 illustrating example tensile stiffness of the example guidewire 100 of FIG. 1. In graph 610, a greater force 612 along the longitudinal length of a guidewire for a same amount of longitudinal displacement 614 corresponds to a greater tensile stiffness. As illustrated in graph 610, guidewire 100 may exhibit greater tensile stiffness than comparable guidewire 602, e.g., such that for a same amount of longitudinal displacement 614, guidewire 100 transfers a greater amount of force 612 along the longitudinal length of guidewire 100 than guidewire 602. The increased tensile stiffness may cause a distal section 103A of guidewire 100 to be more responsive to forces applied by a clinician to a proximal section 103B of guidewire 100 than guidewire 602, e.g., due to the increased transference of force along the longitudinal length of guidewire 100. Varying parameters of openings 108 of guidewire 100 (e.g., radii of curvature, pitch, beam length, mirroring, angular offset angle, length, or width of openings 108) may increase tensile stiffness of guidewire 100 without significantly increasing bending stiffness, e.g., as illustrated in graph 600. For example, a distal portion 110A of elongated body 104 of guidewire 100 may include openings having increased radii of curvature and reduced pitch compared to a proximal portion 110B of elongated body 104 and may increase tensile stiffness while maintaining bending stiffness.

Figure 6C:
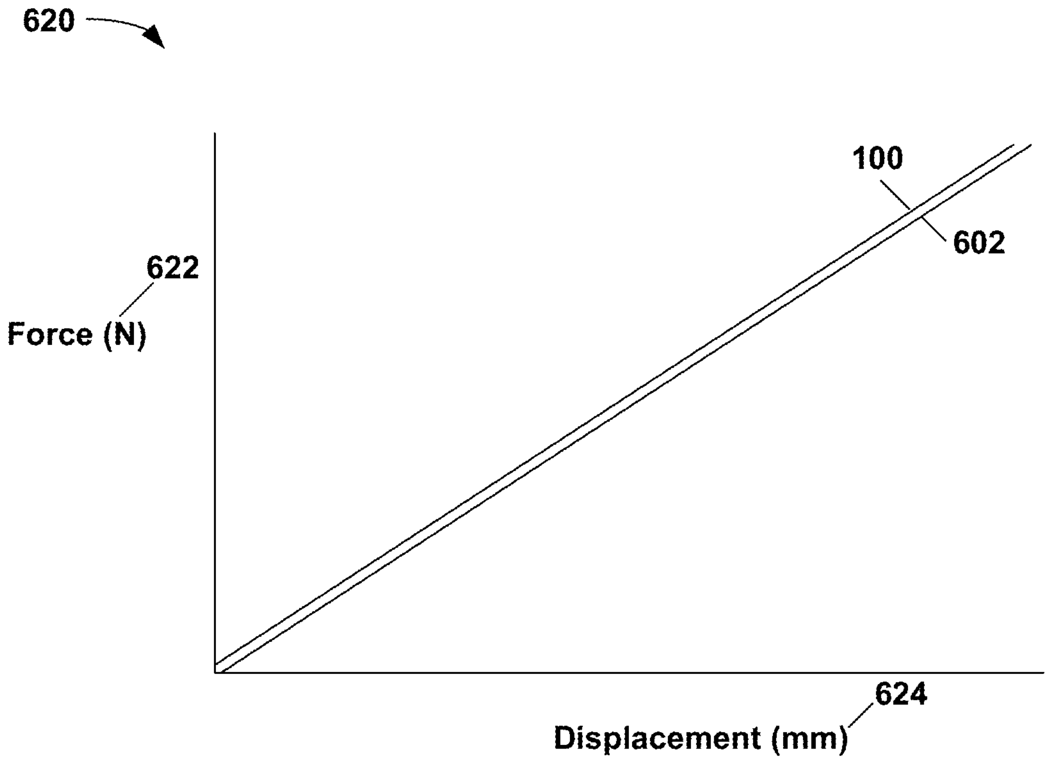
FIG. 6C is a graph illustrating example torque responsiveness of the example guidewire of FIG. 1.

FIG. 6C is a graph 620 illustrating example torque responsiveness of the example guidewire 100 of FIG. 1. Graph 620 illustrates the transference of force 622 in a circumferential direction (e.g., around the longitudinal axis of the guidewire) in response to circumferential displacement 624 of the guidewire about the longitudinal axis of the guidewire. For example, graph 620 illustrates an amount of force 622 transferred along the length of each of guidewire 100, 602 in a circumferential direction in response to rotation, by a clinician, of a proximal section of each guidewire (e.g., of proximal section 103B) by a specific amount of displacement 624. As illustrated in graph 620, guidewire 100 having openings 108, e.g., as previously described herein, may cause guidewire 100 to exhibit a same level of torque responsiveness as a comparable guidewire 602 and an increase in the tensile stiffness of guidewire 100 (e.g., as illustrated in graph 610). For example, the increased radii of curvature and decreased pitch of portions of elongated body 104 may cause guidewire 100 to maintain the same or similar torque responsiveness as guidewire 602 while increasing the tensile stiffness of guidewire 100 relative to guidewire 602.

Figure 7:
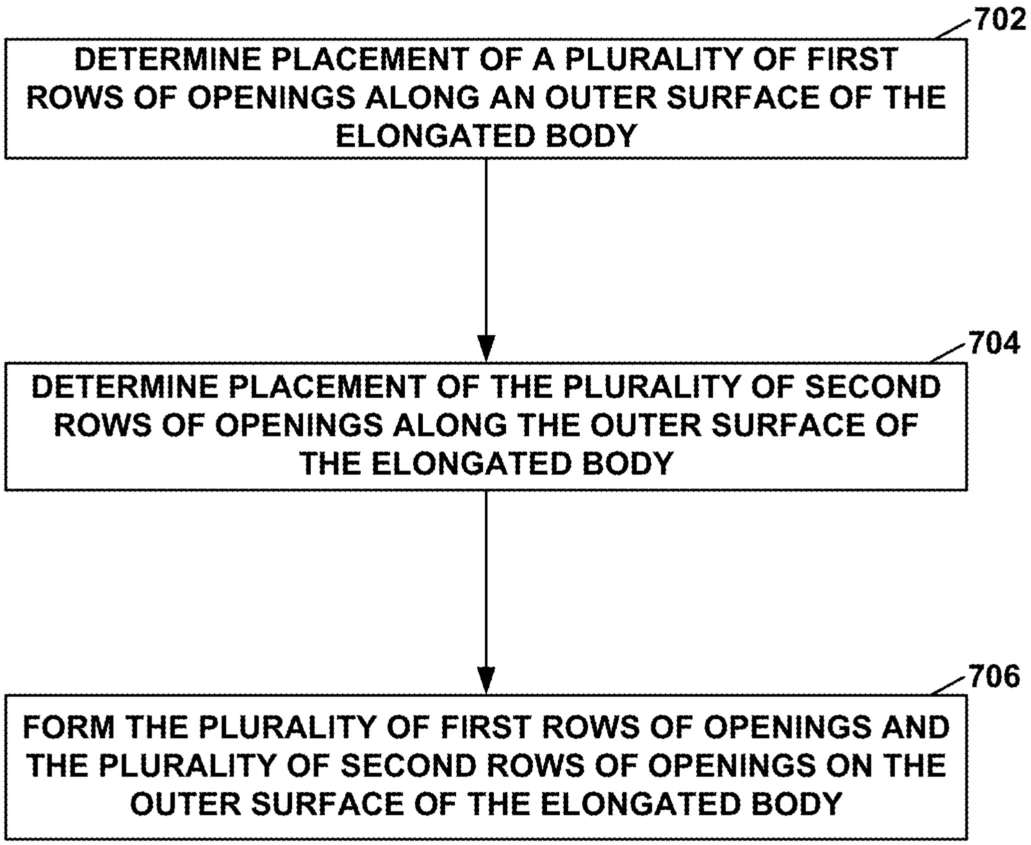
FIG. 7 is a flow diagram illustrating an example method of manufacturing the elongated body of FIG. 1.

FIG. 7 is a flow diagram illustrating an example method of manufacturing elongated body 104 of FIG. 1. While the example method illustrated in FIG. 7 is described herein primarily with respect to an example elongated body 104 having openings 108 similar to openings 302 and 402 as described in FIGS. 3-5, the example method may be applied to elongated body 104 having any other openings, cuts, or voids as described herein.

A manufacturing system may determine placement of a plurality of first rows of openings (e.g., openings 108, 302, 402) along an outer surface 202 of elongated body 104 (702). The plurality of first rows of openings 108 may be collectively referred to herein as a "first group of openings 108." Openings 108 of the first rows of openings 108 may be oriented in a same direction. For example, each opening 108 of the first row of openings 108 may define a concave portion pointing towards one of distal end 104A or proximal end 104B of elongated body 104. The manufacturing system may determine dimensions of each of opening 108 and/or the dimensions between openings 108 and/or retrieve predetermined or pre-set dimensions of openings 108 and/or dimensions between openings 108 and mark the placement of openings 108 on outer surface 202 of elongated body 104 based on the retrieved dimensions.

The dimensions of each of openings 108 may include a length (e.g., chord lengths 223, 306, 406, arc lengths 224, 309, 409), a width (e.g., axial spans 221, 307, 407), a radius of curvature (e.g., radius of curvature 207, 310, 412), and/or a depth (e.g., a thickness normal to a plane of wall 107) of openings 108. The dimensions between openings 108 may include beam lengths between circumferentially adjacent openings 108 (e.g., beam lengths 228, 312, 408), pitches between longitudinally alternating first rows of openings 108 (e.g., pitches 226, 308, 410), angular offset angles (e.g., angular offset angles 230, 304, 404) between longitudinally adjacent patterns (e.g., patterns 235, 311, 411) openings 108, and/or circumferential offset angles (e.g., circumferential offset angles 232). The dimensions of openings 108 and/or the dimensions between openings 108 may vary along elongated body 104. For example, one or more of the dimensions (e.g., beam lengths, pitches) may increase from distal end 104A to proximal end 104B and one or more dimensions (e.g., lengths, radii of curvature, angular offset angles) may decrease from distal end 104A to proximal end 104B.

Based on the determined dimensions, the manufacturing system may determine placement of other openings 108 forming the first rows of openings 108 based on the placement of one or openings 108. The manufacturing system may determine placement of a first opening 108 on distal section 110A of elongated body 104 and determine the placement of the remaining openings 108 defining the first rows of openings 108 based on the determined dimensions and with respect to the location of the first opening 108.

The manufacturing system may determine placement of a plurality of second rows of openings 108 along the outer surface of elongated body 104 (704). The plurality of second rows of openings 108 may be collectively referred to herein as a "second group of openings 108." Each second row of openings 108 may be a mirror image of a first row of openings 108. For example, with respect to the example distal section 110A illustrated in FIG. 3, a first row of openings 108 may include openings 302A and the second row of openings 108 may include openings 302B. In some examples, openings 108 of the first row of openings 108 and the second row of openings 108 may define concave portions pointing towards ends of elongated body 104 and in opposite directions.

Each second row of openings 108 may be longitudinally adjacent to two first rows of openings 108. In some examples, as illustrated in FIGS. 1-4, each second row of openings 108 may be disposed between two first rows of openings 108, thereby longitudinally alternating the first rows of openings 108. Openings 108 of each second row of openings 108 may be circumferentially offset from openings of a longitudinally adjacent first row openings 108, e.g., as previously discussed herein. The manufacturer may determine the placement of the second rows based on the dimensions of the second rows and/or the relationship between the first rows and the second rows.

The first row(s) of openings 108 and second row(s) of openings 108 may form repeating patterns (e.g., patterns 235, 311, and 411) on elongated body 104. In some examples, the manufacturer may determine a plurality of regions 204 on elongated body 104 and place two or more rows of openings 108 (first row(s) and/or second row(s)) in each of regions 204. In some examples openings 108 within each region 204 may have same dimensions and/or may be a same type of openings 108 (e.g., openings 302A, 302B, 402A, 402B). In some examples, each of regions 204 may include openings 108 of two or more types. For example, one region (e.g., region 204A) may include openings 302A and 302B and another region 204 (e.g., region 204N) may include openings 402A and 402B. One or more of regions 204 may be a mirror image of another of regions 204. For example, region 204B may be a mirror image of region 204A relative to a reference plane normal to longitudinal axis 106 of elongated body 104.

The manufacturing system may form the plurality of first rows of openings 108 and the plurality of second rows of openings on outer surface of elongated body 104 (706). In some examples, the manufacturing system may first form elongated body 104 and form openings 108 of the first and second rows of openings 108 on elongated body 104 using any suitable technique. For example, the manufacturing system may form openings 108 via etching, laser cutting, or mechanically cutting via a blade, router, abrasion disk, or the like into a tubular body or other material from which wall 107 of elongated body 104 is formed. In some examples, the manufacturing system may form elongated body 104 using an additive manufacturing technique (e.g., a three-dimensional (3D) printing technique) and define openings 108 during the additive manufacturing.

Figure 8:
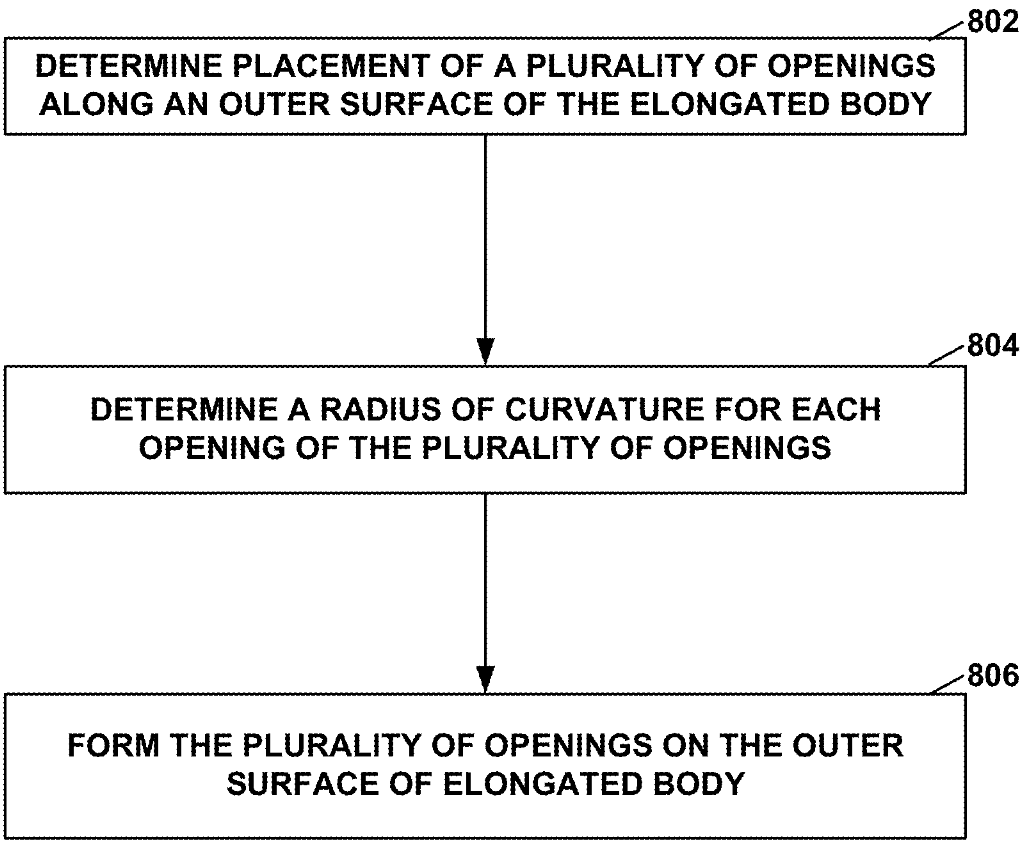
FIG. 8 is a flow diagram illustrating another example method of manufacturing the elongated body of FIG. 1.

FIG. 8 is a flow diagram illustrating another example method of manufacturing elongated body 104 of FIG. 1. While FIG. 8 primarily describes forming openings 108 having varying radii of curvature on elongated body 104, the example methods illustrated in FIG. 8 may be applied to form openings 108 having a same radius of curvature or having other varying dimensions on elongated body 104.

The manufacturing system may determine placement of a plurality of openings 108 along an outer surface of elongated body 104 (802). The manufacturing system may determine the placement of each of openings 108, e.g., as previously described herein. Each of openings 108 may define an arc defining a concave portion. The concave portion may extend towards distal end 104A or proximal end 104B of elongated body 104. Each of openings 108 may define different dimensions than longitudinally distal and/or longitudinally proximal openings 108. In some examples, the dimensions of openings 108 and/or the dimensions between openings 108, e.g., as previously described herein, may vary (e.g., increase or decrease) along elongated body 104 from distal end 104A to proximal end 104B. In some examples, the manufacturing system may arrange openings 108 into circumferential rows of openings 108. In such examples, longitudinally adjacent rows of openings 108 may define concave portions extending towards different ends of elongated body 104.

The manufacturing system may define a plurality of regions 204 over the outer surface of elongated body 104 and place row(s) of openings 108 in each of regions 204. Regions 204 may have a same longitudinal length along longitudinal axis 106 or may have different longitudinal lengths. Each region 204 may have a same number of row(s) of openings 108 and/or a same number of openings 108 as another of regions 204. In some examples, regions 204 may have different numbers of rows of openings 108 and/or different numbers of openings 108. In some examples, openings 204 within each region 204 may have the same dimensions and/or may define the same dimensions between openings 108. In some examples, openings 108 within one region 204 (e.g., region 204A) may have different dimensions or define different dimensions between openings 108 than openings 108 of another region 204 (e.g., region 204B).

The manufacturing system may define a radius of curvature (e.g., radius of curvature 310, radius of curvature 412) for each opening 108 of the plurality of openings 108 (804). The manufacturing system may define the radii of curvature of openings 108 to vary along the length of elongated body 104. For example, the manufacturing system may define the radii of curvature of openings 108 to increase from distal end 104A to proximal end 104B, e.g., to decrease a bending radius of a distal section 110A of elongated body 104. The variation may be linear, non-linear, or discrete (e.g., stepwise changes in the radii of curvature). In some examples, for each row of openings 108, the radii of curvature of openings 108 defining the row may be the same. In some examples, each of regions 204 may include openings 108 defining a different radius of curvature. In such examples, each region 204 may define openings 108 defining larger radii of curvature than a longitudinally proximal region 204. For each opening 108, the manufacturer may select a radius curvature based on a required bending stiffness and/or bending radius of a specific location along elongated body 104 including opening 108. The manufacturer may then form the plurality of openings 108 on the outer surface of elongated body 104 (806), e.g., as previously described herein).

The examples described herein may be combined in any permutation or combination. The disclosure herein describes all of the following examples.

Example 1: a guidewire comprising: a core wire defining a longitudinal axis; and an elongated body extending along the longitudinal axis, the elongated body defining: an inner lumen configured to retain a distal portion of the core wire and a plurality of openings, wherein each opening of the plurality of openings defines an arc defining a radius of curvature and a concave portion facing a distal end of the elongated body or a proximal end of the elongated body, and wherein the radii of curvature of the plurality of openings varies along the longitudinal axis.

Example 2: the guidewire of example 1, wherein the radii of curvature of the plurality of openings decreases from the distal end of the elongated body to the proximal end of the elongated body.

Example 3: the guidewire of any of examples 1 and 2, wherein the radii of curvature of the plurality of openings increases from a proximal portion of the elongated body to the distal end of the elongated body.

Example 4: the guidewire of any of examples 1-3, wherein the plurality of openings comprise a first group of openings disposed at a first location on the elongated body and a second group of openings disposed at a second location on the elongated body, the first group of openings defining a first radius of curvature and the second group of openings defining a second radius of curvature, wherein the second location is more proximal to the first location, and wherein the first radius of curvature is larger than the second radius of curvature so that the elongated body is more resistant to tensile forces at the first location than at the second location.

Example 5: the guidewire of any of examples 1-4, wherein the plurality of openings comprise a first group of openings disposed at a first location on the elongated body and a second group of openings disposed at a second location on the elongated body, the first group of openings defining a first radius of curvature and the second group of openings defining a second radius of curvature, wherein the second location is more distal to the first location, and wherein the first radius of curvature is larger than the second radius of curvature so that the elongated body is more resistant to tensile forces at the first location than at the second location.

Example 6: the guidewire of any of examples 1-5, wherein the elongated body defines a first region and a second region along the longitudinal axis, the second region being longitudinally adjacent to the first region, wherein the first region comprises a first group of openings of the plurality of openings and the second region comprises a second group of openings of the plurality of openings, wherein the openings of the first group define a different radius of curvature than the openings of the second group.

Example 7: the guidewire of any of examples 1-6, wherein the plurality of openings comprises a first group of openings and a second group of openings, wherein each opening of the first group of openings is longitudinally adjacent to and a mirror image of a respective opening of the second group of openings along a plane normal to the longitudinal axis.

Example 8: the guidewire of any of examples 1-7, wherein the plurality of openings comprise a plurality of circumferential rows of openings, wherein each circumferential row of openings is separated from an adjacent circumferential row of openings in a direction of the longitudinal axis, wherein for each circumferential row of openings, circumferentially adjacent openings are separated by a beam length, and wherein the beam lengths increase as the radii of curvature of openings of the corresponding circumferential rows of openings decrease along a length of the elongated body.

Example 9: the guidewire of example 8, wherein the beam lengths decrease in a distal direction along the length of the elongated body.

Example 10: the guidewire of example 8, wherein the beam lengths increase in a distal direction along the length of the elongated body.

Example 11: the guidewire of any of examples 1-10, wherein the plurality of openings comprises a plurality of circumferential rows of openings, wherein longitudinally adjacent circumferential rows of openings are separated by a longitudinal distance, wherein the longitudinal distances vary along a length of the elongated body, wherein the longitudinal distance varies in an opposite direction as the variation in the radii of curvature, and wherein the variation in the longitudinal distances and in the variation in the radii of curvature increases flexibility of a distal portion of the elongated body relative to a proximal portion of the elongated body.

Example 12: the guidewire of example 11, wherein the longitudinal distances decrease in a distal direction.

Example 13: the guidewire of example 11, wherein the longitudinal distances increase in a distal direction.

Example 14: the guidewire of any of examples 1-13, wherein the elongated body comprises a hyptotube.

Example 15: the guidewire of any of examples 1-14, wherein each arc defines an angle less than or equal to 180 degrees.

Example 16: the guidewire of any of examples 1-15, wherein the radius of curvature is 0.5 millimeters (mm) to 3 mm.

Example 17: the guidewire of any of examples 1-16, wherein the variation of the radii of curvature of the plurality of openings increases a tensile strength of a distal portion of the elongated body relative to a proximal portion of the elongated body.

Example 18: the guidewire of any of examples 1-17, wherein the arcs defined by the plurality of openings enable the elongated body to bend in any plane about the longitudinal axis.

Example 19: a method of manufacturing the guidewire of any of examples 1-18, the method comprising: determining placement of the plurality of openings along an outer surface of the elongated body; determining the radius of curvature for each opening of the plurality of openings; and forming the plurality of openings into the outer surface of the elongated body, each opening defining a corresponding determined radius of curvature.

Example 20: a guidewire comprising: a core wire; and an elongated body extending along a longitudinal axis, the elongated body defining: an inner lumen, wherein the distal portion of the core wire is positioned within the inner lumen; and a plurality of openings disposed along the elongated body between a distal end of the elongated body and a proximal end of the elongated body, wherein each opening of the plurality of openings defines an arc define a radius of curvature and extending from a first end to a second end, wherein the first end and the second end are disposed at a same longitudinal position along the elongated body, and wherein for each arc, a center of the arc is disposed at a different longitudinal position than the first end and the second end of the arc, wherein the plurality of openings defines a plurality of rows of openings around a perimeter of the elongated body, wherein longitudinally adjacent rows of openings are separated by a longitudinal distance, and wherein the longitudinal distances between longitudinally adjacent rows and the radii of curvature of the plurality of openings increase or decrease between the distal end and the proximal end.

Example 21: the guidewire of example 20, wherein the radii of curvature of the plurality of openings nonlinearly increases or decreases from the distal end to the proximal end.

Example 22: the guidewire of any of examples 20 and 21, wherein the radii of curvature of the plurality of openings linearly increases or decreases from the distal end to the proximal end.

Example 23: the guidewire of any of examples 20-22, wherein the longitudinal distances decrease in a distal direction along the longitudinal axis, and wherein the radii of curvature of the plurality of openings increase in the distal direction along the longitudinal axis.

Example 24: the guidewire of any of examples 20-23, wherein the longitudinal distances increase in a distal direction along the longitudinal axis and the radii of curvature of the plurality of openings decrease in a distal direction along the longitudinal axis.

Example 25: the guidewire of any of examples 20-24, wherein the elongated body defines a first longitudinal region and a second longitudinal region, wherein the first longitudinal region comprises a plurality of first rows of openings and the second longitudinal region comprises a plurality of second rows of openings, and wherein the plurality of first rows of openings are separated by a first longitudinal distance, wherein the plurality of second rows of openings are separated by a second longitudinal distance, and wherein the first longitudinal distance is larger than the second longitudinal distance.

Example 26: the guidewire of example 25, wherein each first row of openings defines a first radius of curvature, wherein each second row of openings defines a second radius of curvature, and wherein the first radius of curvature is smaller than the second radius of curvature.

Example 27: the guidewire of any of examples 20-26, wherein for each row of openings of the plurality of openings, circumferentially adjacent openings are separated by a beam length, and wherein the beam lengths increase or decrease between the distal end and the proximal end.

Example 28: the guidewire of any of examples 20-27, wherein the plurality of openings comprises a first group of openings and a second group of openings, wherein each opening of the first group of openings is longitudinally adjacent to and a mirror image of a respective opening of the second group of openings along a plane normal to the longitudinal axis.

Various aspects of the disclosure have been described. These and other aspects are within the scope of the following claims.

What is claimed is:

1. A guidewire comprising:

a core wire defining a longitudinal axis; and an elongated body extending along the longitudinal axis, the elongated body defining:

an inner lumen configured to retain a distal portion of the core wire and a plurality of openings, wherein each opening of the plurality of openings defines an arc defining a radius of curvature and a concave portion facing a distal end of the elongated body or a proximal end of the elongated body, and wherein the radii of curvature of the plurality of openings varies along the longitudinal axis.

2. The guidewire of claim 1, wherein the radii of curvature of the plurality of openings decrease from the distal end of the elongated body to the proximal end of the elongated body.

3. The guidewire of claim 1, wherein the radii of curvature of the plurality of openings increase from a proximal portion of the elongated body to the distal end of the elongated body.

4. The guidewire of claim 1, wherein the plurality of openings comprises a first group of openings disposed at a first location on the elongated body and a second group of openings disposed at a second location on the elongated body, the first group of openings defining a first radius of curvature and the second group of openings defining a second radius of curvature, wherein the second location is more proximal to the first location, and wherein the first radius of curvature is larger than the second radius of curvature so that the elongated body is more resistant to tensile forces at the first location than at the second location.

5. The guidewire of claim 1, wherein the plurality of openings comprises a first group of openings disposed at a first location on the elongated body and a second group of openings disposed at a second location on the elongated body, the first group of openings defining a first radius of curvature and the second group of openings defining a second radius of curvature, wherein the second location is more distal to the first location, and wherein the first radius of curvature is larger than the second radius of curvature so that the elongated body is more resistant to tensile forces at the first location than at the second location.

6. The guidewire of claim 1, wherein the elongated body defines a first region and a second region along the longitudinal axis, the second region being longitudinally adjacent to the first region, wherein the first region comprises a first group of openings of the plurality of openings and the second region comprises a second group of openings of the plurality of openings, wherein the openings of the first group define a different radius of curvature than the openings of the second group.

7. The guidewire of claim 1, wherein the plurality of openings comprises a first group of openings and a second group of openings, wherein each opening of the first group of openings is longitudinally adjacent to and a mirror image of a respective opening of the second group of openings along a plane normal to the longitudinal axis.

8. The guidewire of claim 1, wherein the plurality of openings comprise a plurality of circumferential rows of openings, wherein each circumferential row of openings is separated from an adjacent circumferential row of openings in a direction of the longitudinal axis, wherein for each circumferential row of openings, circumferentially adjacent openings are separated by a beam length, and wherein the beam lengths increase as the radii of curvature of openings of the corresponding circumferential rows of openings decrease along a length of the elongated body.

9. The guidewire of claim 1, wherein the plurality of openings comprises a plurality of circumferential rows of openings, wherein longitudinally adjacent circumferential rows of openings are separated by a longitudinal distance, wherein the longitudinal distances vary along a length of the elongated body, wherein the longitudinal distance varies in an opposite direction as the variation in the radii of curvature, and wherein the variation in the longitudinal distances and the variation in the radii of curvature increases flexibility of a distal portion of the elongated body relative to a proximal portion of the elongated body.

10. The guidewire of claim 1, wherein the variation of the radii of curvature of the plurality of openings increases a tensile strength of a distal portion of the elongated body relative to a proximal portion of the elongated body.

11. The guidewire of claim 1, wherein the arcs defined by the plurality of openings enable the elongated body to bend in any plane about the longitudinal axis.

12. The guidewire of claim 1, wherein the first group of openings define a plurality of first circumferential rows of openings, wherein the second group of openings define a plurality of second circumferential rows of openings, wherein each first circumferential row of openings is separated from a first longitudinally adjacent second circumferential row of openings by a first longitudinal distance, and wherein each first circumferential row of openings is separated from a second longitudinally adjacent second circumferential row of openings by a second longitudinal distance, wherein the second longitudinally adjacent second circumferential row of openings is different from the first longitudinally adjacent second circumferential row of openings, and wherein the second longitudinal distance is different from the first longitudinal distance.

13. A guidewire comprising:

a core wire; and an elongated body extending along a longitudinal axis, the elongated body defining:

an inner lumen, wherein the distal portion of the core wire is positioned within the inner lumen; and a plurality of openings disposed along the elongated body between a distal end of the elongated body and a proximal end of the elongated body, wherein each opening of the plurality of openings defines an arc defining a radius of curvature and extending from a first end to a second end, wherein the first end and the second end are disposed at a same longitudinal position along the elongated body, and wherein for each arc, a center of the arc is disposed at a different longitudinal position than the first end and the second end of the arc, wherein the plurality of openings defines a plurality of rows of openings around a perimeter of the elongated body, wherein longitudinally adjacent rows of openings are separated by a longitudinal distance, and wherein the longitudinal distances between longitudinally adjacent rows and the radii of curvature of the plurality of openings increase or decrease between the distal end and the proximal end.

14. The guidewire of claim 13, wherein the radii of curvature of the plurality of openings nonlinearly increase or decrease from the distal end to the proximal end.

15. The guidewire of claim 13, wherein the radii of curvature of the plurality of openings linearly increase or decrease from the distal end to the proximal end.

16. The guidewire of claim 13, wherein the longitudinal distances decrease in a distal direction along the longitudinal axis, and wherein the radii of curvature of the plurality of openings increase in the distal direction along the longitudinal axis.

17. The guidewire of claim 13, wherein the longitudinal distances increase in a distal direction along the longitudinal axis and the radii of curvature of the plurality of openings decrease in a distal direction along the longitudinal axis.

18. The guidewire of claim 13, wherein the first group of openings define a plurality of first circumferential rows of openings, wherein the second group openings define a plurality of second circumferential rows of openings, wherein each first circumferential row of openings is separated from a first longitudinally adjacent second circumferential row of openings by a first longitudinal distance, and wherein each first circumferential row of openings is separated from a second longitudinally adjacent second circumferential row of openings by a second longitudinal distance, wherein the second longitudinally adjacent second circumferential row of openings is different from the first longitudinally adjacent second circumferential row of openings, and wherein the second longitudinal distance is different from the first longitudinal distance.

19. A guidewire comprising:

a core wire defining a longitudinal axis; and an elongated body extending along the longitudinal axis, the elongated body defining:

an inner lumen, wherein a distal section of the core wire is positioned within the inner lumen; and a plurality of openings between a distal end of the elongated body and a proximal end of the elongated body, wherein each opening of the plurality of openings defines an arc extending from a first end to a second end, wherein a center of the arc is longitudinally offset from the first and second ends, wherein the arc defines a radius of curvature, and wherein the plurality of openings comprises:

a first group of openings disposed around a perimeter of the elongated body, the first group of openings defining a plurality of first circumferential rows of openings, and wherein the radii of curvature of the first group of openings varies along the longitudinal axis; and a second group of openings disposed around the perimeter, the second group of openings defining a plurality of second circumferential rows of openings, wherein each opening of the second group of openings is longitudinally adjacent to and is a mirror image of a respective opening of the first group of openings relative to a plane normal to the longitudinal axis, wherein each first circumferential row of openings is separated from a first longitudinally adjacent second circumferential row of openings by a first longitudinal distance, and wherein each first circumferential row of openings is separated from a second longitudinally adjacent second circumferential row of openings by a second longitudinal distance, wherein the second longitudinally adjacent second circumferential row of openings is different from the first longitudinally adjacent second circumferential row of openings, and wherein the second longitudinal distance is different from the first longitudinal distance.

20. The guidewire of claim 19, wherein the first longitudinal distance and the second longitudinal distance increase from the distal end to the proximal end.

* * * * *